US008236496B2

(12) United States Patent
Russwurm et al.

(10) Patent No.: US 8,236,496 B2
(45) Date of Patent: Aug. 7, 2012

(54) USE OF GENE ACTIVITY CLASSIFIERS FOR THE IN VITRO CLASSIFICATION OF GENE EXPRESSION PROFILES OF PATIENTS WITH INFECTIOUS/NON-INFECTIOUS MULTIPLE ORGAN FAILURE

(75) Inventors: Stefan Russwurm, Jena (DE); Konrad Reinhart, Jena (DE)

(73) Assignee: SIRS-Lab GmbH, Jena (DE)

( * ) Notice: Subject to any disclaimer, the term of this patent is extended or adjusted under 35 U.S.C. 154(b) by 798 days.

(21) Appl. No.: 11/909,372

(22) PCT Filed: Mar. 16, 2006

(86) PCT No.: PCT/EP2006/060780
§ 371 (c)(1),
(2), (4) Date: Feb. 23, 2009

(87) PCT Pub. No.: WO2006/100203
PCT Pub. Date: Sep. 28, 2006

(65) Prior Publication Data
US 2009/0325152 A1 Dec. 31, 2009

(30) Foreign Application Priority Data
Mar. 21, 2005 (DE) .......................... 10 2005 013 013

(51) Int. Cl.
C12Q 1/68 (2006.01)
C12P 19/34 (2006.01)
(52) U.S. Cl. ....................................... 435/6.1; 435/91.2
(58) Field of Classification Search ................. 435/91.2, 435/6
See application file for complete search history.

(56) References Cited

U.S. PATENT DOCUMENTS

| 5,830,679 A | 11/1998 | Bianchi et al. |
| 2001/0051344 A1 | 12/2001 | Shalon et al. |
| 2003/0194752 A1 | 10/2003 | Anderson et al. |
| 2004/0106142 A1 | 6/2004 | Ivey et al. |
| 2006/0134685 A1 | 6/2006 | Zipfel et al. |
| 2008/0070235 A1 | 3/2008 | Russwurm et al. |
| 2008/0286763 A1 | 11/2008 | Russwurm |

FOREIGN PATENT DOCUMENTS

| DE | 10041215 A1 | 10/2001 |
| WO | 03002763 A1 | 1/2003 |
| WO | 2004043236 A2 | 5/2004 |

OTHER PUBLICATIONS

Freezor et al., Clinical Infectious Disease, vol. 41, S427-35, Sep. 2005.*
Gitig, Diana, Genetic Engineering & Biotechnology News, vol. 31, No. 20, pp. 1-3, Nov. 15, 2011.*
Enard et al. (Science 2002 vol. 296 p. 340).
Wu (Journal of pathology 2001 vol. 195 p. 53).
Newton et al (Journal of Computational Biology 2001 vol. 8 p. 37).
Hynninen et al. (Shock 2003 vol. 20 p. 1).
Perry et al. (Intensive Care Med 2003 VO. 29 p. 1245).
Riedemann et al. (Journal of Clinical Investigation Jul. 2002 vol. 110 p. 101).
Cobb, J. Perren. Crit Care Med 2002 vol. 30, No. 12. p. 2711-2721.
Ko, J.L. et al.: "Molecular cloning and expression of a fungal immunomodulatory protein, FIP-FVE, from *Flammulina velutipes*", J. Formos Med Assoc, 96:7, 517-524 (1997).
Hoshikawa, Y. et al.: "Hypoxia induces different genes in the lungs of rats compared with mice", Physiol Genomics (2003) 12 : 209-219.
Cheung, V.G. et al.: "Natural variation in human gene expression assessed in lymphoblastoid cells", Nature Genetics (2003), vol. 33, pp. 422-425.
Thisted, Ronald A. et al.: "What is a P-value?", (1998) available from http://www.stat.uchicago.edu/thisted, printed pp. 1-6.
"Details for HG-U95AV2:2024_S_AT" Internet Citation [Online], Oct. 1, 2004, pp. 1-3, XP007907827, found on the internet: URL: https://www.affymetrix.com/analysis/netaffx/fullrecord.affx?pk=H>, found on Mar. 20, 2009.
Haslinger, Christian et al.: "Microarray Gene Expression Profiling of B-Cell Chronic Lymphocytic Leukemia Subgroups Defined by Genomic Aberrations and VH Mutation Status", Journal of Clinical Oncology, American Society of Clinical Oncology, US, vol. 22, No. 19, Oct. 1, 2004, pp. 3937-3949, XP009114229.
Tulzo et al. "Early Circulating Lymphocyte Adoptosis in Human Septic Shock is Associated With Poor Outcome" Shock 2002, vol. 18, p. 487-494.
Japanese Office Action and English Translation Thereof, Apr. 26, 2011.
"Method of Measuring Procalcitonin" Examination and Technology 2002, vol. 30, No. 7, pp. 569-570.
Cobb, et al. "Sepsis Gene Expression Profiling: Murine Splenic Compared With Hepatic Responses Determined by Using Complementary DNA Microarrays" Crit. Care Med., 2002, vol. 30, pp. 2711-2721.
Liu, et al. "Gene Expression Profiles in Human Nasal Polyp Tissues Studied by Means of DNA Microarray" J. Allergy Clin. Immunol., 2004, vol. 114, pp. 783-790.
Office Action in corresponding chinese application procedure, Dec. 18, 2009.

(Continued)

Primary Examiner — Gary Benzion
Assistant Examiner — Cynthia Wilder
(74) Attorney, Agent, or Firm — Patent Central LLC; Stephan A. Pendorf

(57) ABSTRACT

The present invention relates to the use of gene activity markers for classification of patients suffering from infectious and non-infectious multiple organ failure, respectively.

The present invention in particular relates to gene activity markers for classification of patients as "not infected without multiple organ failure" or as "not suffering from infectious multiple organ failure" or as "suffering from infectious multiple organ failure", the gene activity markers being polynucleotides selected from the group consisting of: SEQ ID I.1, SEQ ID I.2, SEQ ID I.3, SEQ ID I.4, SEQ ID I.5, SEQ ID I.6, SEQ ID I.7, SEQ ID I.8 and SEQ ID I.9 or partial sequences thereof.

3 Claims, 3 Drawing Sheets

OTHER PUBLICATIONS

EMBL N32857, Publication Date: Jan. 13, 1996.
EMBL N32853, Publication Date: Jan. 13, 1996.
EMBL N32495, Publication Date: Jan. 13, 1996.
EMBL A1701077, Publication Date: Jun. 4, 1999.
EMBL M87790, Publication Date: Mar. 10, 1992.
EMBL A1559317, Publication Date: Mar. 25, 1999.
EMBL N34897, Publication Date: Jan. 19, 1996.
EMBL AA907084, Publication Date: Apr. 14, 1998.
EMBL N45223, Publication Date: Feb. 17, 1996.
Van De Vijver, M.J. et al.: "A gene-expression signature as a predictor of survival in breast cancer" N. Engl. J. Med (2002) 347 (25) 1999-2009.

* cited by examiner

USE OF GENE ACTIVITY CLASSIFIERS FOR THE IN VITRO CLASSIFICATION OF GENE EXPRESSION PROFILES OF PATIENTS WITH INFECTIOUS/NON-INFECTIOUS MULTIPLE ORGAN FAILURE

BACKGROUND OF THE INVENTION

1. Field of the Invention

The present invention relates to the use of gene activity markers for the classification of patients suffering from infectious and non-infectious multiple organ failure, respectively.

The invention further relates to the use of said gene activity classificators as stored value parameters in devices used for in vitro diagnosis for patients with infectious and non-infectious multiple organ failure. Furthermore, the invention relates to a device for in vitro diagnosis of patients suffering from infectious multiple organ failure and non-infectious multiple organ failure, respectively.

Further, the invention relates to the use of gene activity marker/classificators for the classification of gene expression profiles of patients for assessing the therapeutic effects of active substances for the treatment of infectious multiple organ failure and non-infectious multiple organ failure, respectively.

2. Description of the Related Art

Despite advances in pathophysiological understanding and the supportive treatment, the multiple organ failure syndrome (MOFS) and multiple organ failure (MOF), respectively, is the most frequent cause of death in patients in intensive care and is continuously increasing worldwide. The consequences of this development are not only considerable to the individual patient but they also have enormous effects on the costs of the public health care systems and the medical progress in many fields of medicine.

Multiple organ failure is defined as the failure of two or more vital organ systems occurring simultaneously or within a short time period. The multiple organ failure syndrome (MOFS) precedes the MOF as initial organ insufficiency [1]. Today's definition of multiple organ failure is the dysfunction of two or more organs occurring simultaneously or within a short period of time, whereas a chronically persistent organ failure can be ruled out [2]. The prognosis of MOF is closely related to the number of the involved organ systems. If one organ fails, the mortality rate within 24 hours is 22%; after 7 days it is 41%. In the case of failure of three organ systems, the mortality increases on the first day to 80% and after 4 days to 100% [3].

For the clinical scoring of the degree of severity in MOFS and MOF, the multiple organ failure score (MOF-score) of GORIS et al. [4] or, alternatively, the sepsis related organ failure assessment (SOFA) score are routinely used [5]. The MOF score renders a quick and clinically simple classification of the organ function in three grades possible. In the clinical literature, a MOF score>4 is routinely described as MOF [6]. SOFA score is a point system quickly scoring the clinical assessment of the function, of the following organ systems: respiration (lung), coagulation, liver, cardiovascular system, central nervous system and kidney. Four grades are used in this scoring system.

Clinically, the MOF runs in three stages [7]:
1. Organ in shock: The triggering pathophysiological mechanism is a perfusion deficiency of very different genesis. This happens within hours and does not yet lead to permanent damages.
2. Organ dysfunction: If the persistent perfusion deficit persists for the next few days, this will lead to the development of SIRS (Systemic inflammatory Response Syndrome, classified according to [8]) with local oedema and cell damages. This stage is called multiple organ dysfunction syndrome (MODS).
3. Organ failure: The persistent perfusion deficit leads to stasis in the splanchnic area which leads to a superinfection and translocation of endotoxines from the intestines. This leads to a potentiation of the clinical symptoms and to the complete picture of the sepsis. The organ dysfunction becomes an organ failure.

MODS and MOF are clinical pictures with a complex pathophysiology. The exact molecular causes for the development and the complexity of the immunological-inflammatory host response to severe infection and trauma that can trigger SIRS and the corresponding cardiocirculatory effects are not completely understood up to the present day [9].

MODS and MOF can be both of infectiologic and non-infectiologic genesis. MODS and MOF routinely develop as a clinical important complication in patients with sepsis, after a shock that was caused by trauma, with patients after surgeries where the heart-lung machine was used, after organ transplantation, and others (FIG. 1). An important pathogenetic mechanism for the development of MODS and MOF is the development of a systemic inflammatory syndrome (SIRS, [8]). The pathophysiological processes initiated in the framework of SIRS do not only involve all components of the immune system, but interfere with all levels of the cardiocirculatory system and are not restricted to myocardial depression and vasodilation. The cardiocirculatory changes in particular on the microcirculation level form the common final distance and result in a tissue hypoxia which is considered an important cofactor in the pathogenesis of multiple organ failure.

FIG. 1 shows an exemplary description of the most important mechanisms of the development of MODS and MOF by today's standards [10]: It seems that an overactive immune system plays a decisive role in the development of multiple organ failure. In this context, the endothelium plays a central key role by secretion of cytokines and by imparting leukocyte adhesion. Signal transduction cascades are activated in the endothelial cells leading to the expression and activation of transcription factors.

The reason why there is still no sensitive/specific diagnostic being able to differentiate between infectious and non-infectious causes is the still incomplete knowledge of the early stage processes in MODS and MOF. New types of biomarkers and diagnostics, now even on a gene expression level, may provide the essential diagnostic information for early diagnosis of multiple organ failure as well as for the differentiation between infectious and non-infectious causes of MODS and MOF. Additionally, they are important in contributing to the clarification of the pathophysiologic mechanisms of systemic inflammations.

The precursory symptoms that are often used in clinical practice, as fever, leukocytosis, tachycardia and tachypnea are completely unspecific for the diagnosis of MODS or MOF as well as for differentiating between infectious and non-infectious causes of MODS and MOF. Parameters detecting irregularities in microcirculations at an early stage, as for example changes in the pH of the intestinal mucosa [11] and lactate level in the capillary bed [12, 13], emerging of a respiratory insufficiency the cause of which is not in the lung [2], the ascent of the leukocyte elastase [14,15], the height of the neopterine level [16], the activation of polymorphnuclear leukocytes and the height of the IL-6-level [17] are suitable as early parameters for the later development of MODS and MOF only to a limited extend, but they cannot contribute to the differentiation between infectious and non-infectious causes of MODS and MOF. Thus, there is urgent need for novel diagnostic methods for improving the capacity of the person skilled in the art to differentiate at an early stage between non-infectious and infectious MODS or MOF and to make predictions on how the patient will respond to specific treatments.

However, it is exactly the differentiation between infectious and non-infectious causes of MODS and MOF which is of utmost medicinal importance, as for example antibiotics may be used more efficiently with this differentiation, this contributing to considerable cost savings as well as to the avoidance of side effects caused by the unspecific application of antibiotics. In the case of non-infectious MODS or MOF it is, moreover, possible to avoid time and people-intensive diagnostic measures that are very stressful for the patient (e.g. transport to CT/MRI) for identification of the respective site of infection, the realization of comprehensive microbiological methods (e.g. examination of blood cultures for which the patient also must deliver great amounts of blood) but also the risky exchange of all plastics material connected with the patient, such as venous catheter, etc. Vice versa the quick identification of infectious causes of MODS or MOF can ensure that these measures are taken quickly and mortality can, therefore, be reduced.

Technological advances, in particular the development of microarray technology, make it now possible for the person skilled in the art to simultaneously compare 10 000 or more genes and their gene products. The use of such microarray technologies can provide information regarding the status of health, regulatory mechanisms, biochemical interactions and signal transmitter networks. As the comprehension how an organism reacts to infections is improved this way, this should facilitate the development of enhanced modalities of detection, diagnosis and therapy of infectious disorders.

Microarrays have their origin in "Southern blotting" [19], which represented the first approach to immobilizing DNA-molecules so that it can be addressed three-dimensionally on a solid matrix. The first micro arrays consisted of DNA-fragments, frequently with unknown sequence, and were applied dotwise onto a porous membrane (normally nylon). Routinely, cDNA, genomic DNA or plasmid libraries were employed and the hybridized material was labelled with a radioactive group [20-22].

Nowadays, the use of glass as substrate and fluorescence for detection together with the development of new technologies for the synthesis and for the application of nucleic acids in very high densities makes it possible to miniaturize the nucleic acid arrays. At the same time, the experimental throughput and the information content were increased [23-25].

The first explanation for the applicability of microarray technology was obtained through clinical trials in the field of cancer research. Here, expression profiles proofed to be valuable with regard to identification of activities of individual genes or groups of genes, which correlate with certain clinical phenotypes [26]. Many samples of individuals with or without acute leukaemia or diffuse B-cell lymphoma were analyzed and gene expression labels (RNA) were found and subsequently employed for the clinically relevant classification of these types of cancer [26,27]. Golub et al. found out that an individual gene is not enough to make reliable predictions, while, however, predictions based on the change in transcription of 53 genes (selected from more than 6000 genes, which were present on the arrays) are highly accurate [26].

It is known from WO 03/002763 that determination of gene expression profiles using microarrays basically can be used for the diagnosis of sepsis and sepsis-like conditions.

The Applicant's German Patent Applications DE 103 40 395.7, DE 103 36 511.7, DE 103 150 31.5 and 10 2004 009 952.9 describe that gene expression profiles, which are for example obtainable by means of the microarray technology, are, in principle, usable for the diagnosis of SIRS, generalized inflammatory inflammations, sepsis and severe sepsis. These applications are herein incorporated by reference.

It is known from Feezor et al. [28] that the gene activities of patients which developed SIRS with multiple organ dysfunction syndrome (MODS) as a consequence of their surgical treatment differ from those of patients who developed SIRS without MODS as a consequence of the same surgical treatment. However, these studies do not allow a statement on the differentiation of non-infectious MOF compared to infectious MOF, as no infection was detected in these patients.

For the classification of gene expression profiles, various methods and their use for gene expression data, for example linear and quadratic discrimination analyses, Compound Covariant Predictor, Nearest Neighbor Classification, Classification Trees or Support Vector Machines have already been described [26, 29, 30, 31, 32]. A general survey on the use of classification methods for the analysis of gene expression data is shown in [33].

It is the object of the classification methods to develop multivariant classificators which allow predictions on whether a new data set belongs to a class. Thus, patients may, for example, be classified by means of classificators into responders or non-responders regarding their response to a special treatment.

Generally, classificators are developed in three steps:
1. Selection of statistically relevant features from a large data set. For gene expression analyses, univariant tests are used as a first step to select the statistically relevant genes from various classes, based on their expression pattern.
2. Determination of the classificators by means of different classification methods, at the end of which a training set of classificators is provided.
3. Validation of this training set by means of new, non-classified test sets of gene expression profiles, and optimization of the training set.

WO 2004/108957 generally describes the classification of biomarkers (nucleic acids) and their use for the diagnosis of SIRS and sepsis, respectively. The classification and/or use of biomarkers for the diagnosis of infectious and non-infectious multiple organ failure, respectively, is not described.

The prior German Patent Application No. 102004 049897.041 describes for the first time gene activity markers for differentiating between infectious and non-infectious multiple organ failure. This application describes the use of 1297 different genes for in vitro diagnosis of patients suffering from infectious and non-infectious multiple organ failure, respectively.

BRIEF SUMMARY OF THE INVENTION

The present invention goes beyond the state of the art described in DE 102004049897.041, in that it was found by means of specific tests of the gene expression profiles from patient samples, which gene activities are suitable as classificators for the in vitro diagnosis for differentiating between non-infectious and infectious multiple organ failure.

The invention disclosed in the present patent application is based on the perception that gene activity classificators can be used to classify the gene expression profiles of patients with non-infectious and infectious MOF, respectively. The use of these classificators is not possible with the clinical parameters conventionally used for diagnosis, however, it is very important for the initiation of a specialized therapy in intensive care.

Thus, it is the object of the present invention to use gene activity classificators for differentiating between non-infected patients without multiple organ failure, non-infectious multiple organ failure and infectious multiple organ failure.

The object of the present infection is achieved by gene activity markers, a method for classification of patients, a microarray according and a device which will now be explained in greater detail.

In the following, the term "ITS-control" is used for patients treated in intensive care, who, however, had no infection detected and multiple organ failure diagnosed.

The present invention in particular relates to the use of gene activity classificators, based on which gene expression profiles obtained in vitro from a patient sample are classified into non-infectious and infectious multiple organ failure.

Using the classificators, the present invention is further usable for assessing the course of patients suffering from non-infectious and infectious causes of multiple organ failure during therapy.

The gene activity classificators according to the present invention are further usable as inclusion or exclusion criterion of patients with non-infectious or infectious causes of multiple organ failure in clinical trials of the stages 2-4.

BRIEF DESCRIPTION OF THE SEVERAL VIEWS OF THE DRAWINGS

The present invention is illustrated by way of example and not limitation in the accompanying drawings in which.

DETAILED DESCRIPTION OF THE INVENTION

Figure 1:
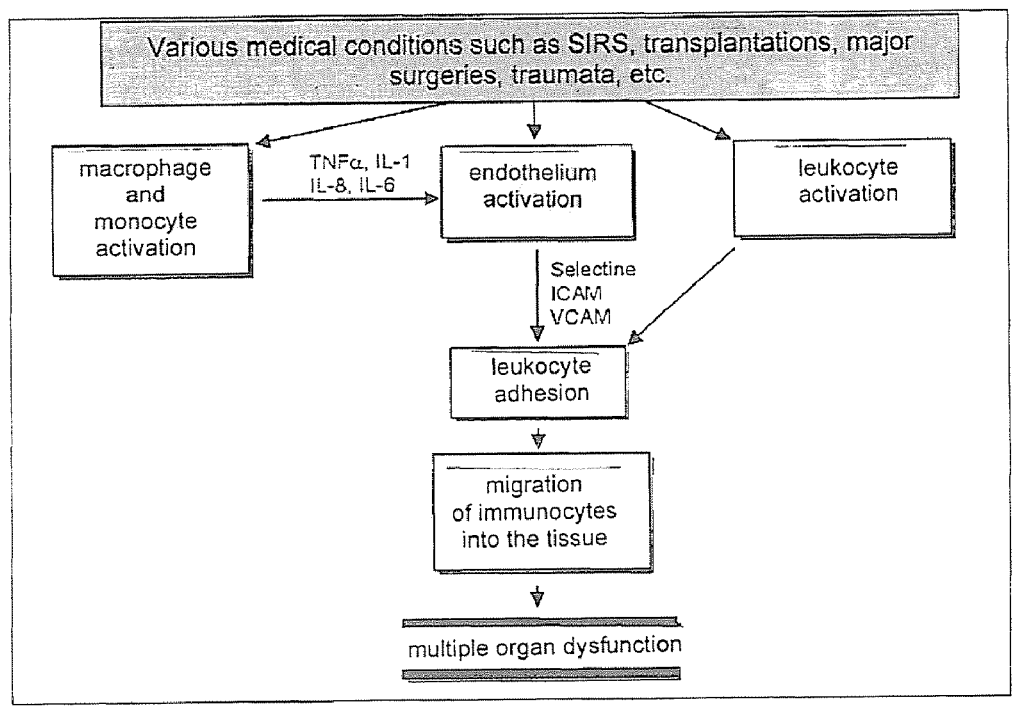
FIG. 1 shows the pathologic course of multiple organ failure starting from different medical conditions.

A preferred embodiment of the present invention relates to the provision of gene activity classificators for further electronic processing as well as for the production of software for the description of the individual prognosis for a patient, for diagnosis and/or patient data management systems. In this context, the gene activity classificators are used as basis for automatically assessing the gene expression profiles to be examined in vitro in diagnostic devices. Here, the gene expression classificators are stored as value parameters in software, an integrated circuit, an EPROM or other technical means known to the person skilled in the art for storage of value parameters.

Another preferred embodiment of the invention relates to a device using the gene activity classificators stored as value parameters to allow for an in vitro diagnosis of patients with non-infectious and infectious multiple organ failure. In addition to the gene activity classificators stored as value parameters, said device includes a means to compare non-classified gene expression profiles of patient samples with the stored gene activity classificators and to output the corresponding result as technical display. This can, for example, be realized by electronic processing of the value parameters—transformed to electronic signals—of the gene activity classificators and comparing with the electronic signals won from the gene expression profiles to be examined. The result of this comparison is the classification of the gene expression profile to be examined into one of the classes of non-infectious multiple organ failure and infectious multiple organ failure, respectively. Analog and/or digital displays, such as score systems (similar to the APACHE or SOFA Score already used in in vitro diagnostics) or in silico gels, acoustic signals or other methods known to the person skilled in the art are used as the technical display.

In a preferred embodiment, this device also enables the generation of gene expression profiles for comparison with the stored gene activity classificators. For this purpose, this device consists of a module for the sample preparation of the patient sample obtained in vitro, a module for the hybridization of the patient sample with gene activity probes derived from the gene activity classificators, a module for reading out the hybridization signals, another module for image analysis of the readout hybridization signals, a module enabling the automatic comparison with the stored gene activity classificators, as well as a module allowing the display of the resulting comparison. It is self-evident for the person skilled in the art that not all modules have to be combined in said device, depending on the level of automation. Examples for devices already enabling an automatic/semi-automatic creation of gene expression profiles are the Light Cycler of the company Roche, the Smart Cycler of Cepheid or the AP system of Clondiag Chip Technologies.

Further, the person skilled in the art knows that all other methods for analyses of differential gene expression may be used as an alternative to the method for generating gene expression profiles by the microarray technology described in the present patent application.

The gene activity classificators according to the present invention may also be used for the creation of "in silico" expert systems and/or for "in silico" modulation of cellular ways of signal transfer.

As gene activity classificators according to the present invention, gene and/or gene fragments are used, selected from the group consisting of SEQ ID NO: 1 to SEQ ID NO: 9, as well as gene fragments thereof with 5-2000 or more, preferably 20-200, more preferably 20-80 nucleotides.

These sequences with SEQ ID NO: 1 to SEQ ID NO: 9 are incorporated by the scope of the present invention and they are in detail disclosed in the enclosed sequence listing comprising 9 sequences which is, thus, part of the description of the present invention and, therefore, also part of the disclosure of the invention. In the sequence listing the individual sequences with SEQ ID NO: 1 to SEQ ID NO: 9 are further assigned to their GenBank Accession No. (website: www.ncbi.nlm.nih.gov/).

In this context, also hybridizable synthetic analogues of the listed probes may be used.

The use of insertion-, deletion or nucleotide replacement mutants of sequences SEQ ID NO: 1 to SEQ ID NO: 9 is also possible for the purposes of the present invention, as long as these mutations do not substantially change the sequences' hybridizing behavior for the purposes of the present invention. Whenever reference is made to gene activity markers in the present invention, such mutations are also included.

In another embodiment, the gene activity classificators SEQ ID NO: 1 to SEQ ID NO: 9 are linked to logical selection rules for the classification of gene expression profiles of patient samples with non-infectious and infectious multiple organ failure, respectively, according to table 1.

TABLE 1

Selection rules for the classification ITS-control, non-infectious and infectious multiple organ failure, respectively

| Class | ITS-control | Non-infectious multiple organ failure | Infectious multiple organ failure |
|---|---|---|---|
| Classifiers | (SEQ-ID No. I.1)↑ and (SEQ-ID No. I.3)↓ or (SEQ-ID I.2)↑ and (SEQ-ID No. I.4)↓ | (Seq-ID I.3)↑ and (Seq-ID I.6)↓ or (SEQ-ID No. I.4)↑ and (SEQ-ID No. I.5)↓ | (SEQ-ID I.5)↑ and (SEQ-ID I.7)↓ or (SEQ-ID No. I.8)↑ and (SEQ-ID No. I.9)↑ |

↑ overexpressed gene activity,
↓ underexpressed gene activity

Another embodiment of the present invention is characterized in that the genes or gene fragments and/or sequences derived from their RNA are replaced by synthetic analogues, aptamers, as well as peptide nucleic acids.

Another embodiment of the present invention is characterized in that the sample is selected from: body fluids, in particular blood, liquor, urine, ascitic fluid, seminal fluid, saliva, puncture fluid, cell content, or a mixture thereof.

Another embodiment of the present invention is characterized in that cell samples are subjected to a lytic treatment, if necessary, in order to release their cell contents.

It is obvious to the person skilled in the art that the individual features of the present invention presented in the claims can be combined with each other in any desired way.

Gene activity classifiers as used in the present invention include all derived DNA-sequences, partial sequences and synthetic analogues (for example peptido-nucleic acids, PNA). The description of the invention referring to the determination of the gene expression on RNA level is not supposed to be a restriction but only an exemplary application of the present invention.

The description of the invention referring to blood is only an exemplary embodiment of the present invention. The term biological fluids as used in the present invention is meant to include all human body fluids.

Further advantages and features of the present invention will become apparent from the description of a working example as well as from the drawing.

FIG. 1 shows the pathologic course of multiple organ failure starting from different medical conditions.

Working Example

Study on the generation and validation of gene activity classificators for classification of gene expression profiles of patient samples into one of the following classes: ITS-control, non-infectious multiple organ failure or infectious multiple organ failure.

Measurement of Differential Gene Expression as Basis for the Training Set:

Whole blood samples of a total of 57 patients treated in surgical intensive care units were tested for measuring differential gene expression to differentiate between non-infectious and infectious causes of multiple organ failure. The complete gene expression data formed the basis for generating the training set of the gene activity classifiers.

Whole blood samples were taken from 31 patients who developed an infectious MOF [classified according to 8] during intensive care.

Furthermore, whole blood samples were taken from 26 patients who developed a non-infectious MOF [classified according to 8] during intensive care.

Additionally, whole blood samples were taken from 18 patients who were subject to intensive care (in the following: ITS-controls).

Reference samples were total RNA from SIG-M5 cell lines.

Selected characteristics of the three patient groups are shown in table 2. Information includes age, sex, as well as the SOFA-score as a measure for the function of the organ systems. In addition, the plasma protein levels of procalcitonine (PCT) and CRP as well as the number of leukocytes of the patients are given.

Each patient sample was co-hybridized with the reference sample on a microarray.

TABLE 2

Data of the group of patients

| | ITS-controls | Non-infectious MOF | Infectious MOF |
|---|---|---|---|
| Number of Patients | 18 | 26 | 31 |
| Sex m/f | 16/2 | 15/11 | 17/14 |
| Age [years] | 65 (15) | 69 (10) | 60 (17) |
| APACHE-II Score [points] | 10* (2.8) | 14.9 (3.4) | 14 (10) |
| SOFA Score [points] | 3.4* (1.7) | 8* (3) | 10* (3) |
| Number of organ dysfunctions | — | 3 (1) | 3 (1) |
| PCT [ng/ml] | 0.56* (0.8) | 3.8 (6.7) | 3.1 (7.7) |
| CRP [µg/l] | 68.5* (27.5) | 80.2* (90.2) | 188* (168) |
| WBC [no/l] | 8,088* (3,554.2) | 12,300 (6,925) | 13,200 (8,150) |

*p < 0.05

Experimental Description:

After drawing whole blood, the total RNA of the samples was isolated using the PAXGene Blood RNA kit according to the manufacturer's (Qiagen) instructions.

Cell Cultivation

For cell cultivation (control samples) 19 cryo cell cultures (SIGM5) (frozen in liquid nitrogen) were used. The cells were each inoculated with 2 ml Iscove's medium (Biochrom AG) supplemented with 20% fetal calf serum (FCS). Subsequently, the cell cultures were incubated in 12 well plates for 24 hours at 37° C. in 5% CO2. Subsequently, the content of the 18 wells was parted in 2 parts with the same volume so that finally 3 plates of the same format (36 wells in total) were available. Afterwards, the cultivation was continued under the same conditions for 24 hours. Afterwards, the resulting cultures of 11 wells of each plate were combined and centrifuged (1000×g, 5 min, ambient temperature). The supernatant was removed and the cell pellet was dissolved in 40 ml of the above mentioned medium. These 40 ml of dissolved cells were distributed in equal shares in two 250 ml flasks and incubated after adding 5 ml of the above-mentioned medium. 80 µl of the remaining 2 ml of the two remaining plates were placed in empty wells of the same plates that had previously been prepared with 1 ml of the above-mentioned medium. After 48 hours of incubation, only one of the 12 well plates was processed as follows: 500 µl were extracted from each well and combined. The resulting 6 ml were introduced into a 250 ml flask comprising approximately 10 ml of fresh medium. This mixture was centrifuged 5 minutes with 1000×g at ambient temperature and dissolved in 10 ml of the above-mentioned medium. The following results were obtained by subsequent counting of cells: $1.5 \times 10^7$ cells per ml, 10 ml total volume, total number of cells: $1.5 \times 10^8$. As the number of cells was not yet sufficient, 2.5 ml of the above-mentioned cell suspension was introduced into 30 ml of the above-mentioned medium in a 250 ml (75 cm$^2$) flask (4 flasks in total). After 72 hours of incubation 20 ml of fresh medium were added to each flask. After the subsequent incubation of 24 hours, the cells were counted as described above. The total amount of cells was $3.8 \times 10^8$ cells. In order to obtain the desired number of cells of $2 \times 10^6$ cells, the cells were resuspended in 47.5 ml of the above mentioned medium in 4 flasks. After the incubation time of 24 hours, the cells were centrifuged and washed two times with phosphate buffer in absence of $Ca^{2+}$ and $Mg^{2+}$ (Biochrom AG).

The isolation of the total RNA is performed by means of NucleoSpin RNA L Kits (Machery&Nagel) according to the manufacturer's instructions. The above described process was repeated until the necessary number of cells was obtained. This was necessary to obtain the necessary amount of 6 mg total RNA corresponding to an efficiency of 600 µg RNA per 108 cells.

Reverse Transcription/Labelling/Hybridization

After drawing whole blood, the total RNA of the samples was isolated and tested for quality using the PAXGene Blood RNA kit (PreAnalytiX) according to the manufacturer's instructions. 10 µg total RNA were aliquoted from each sample and transcribed with 10 µg total RNA from SIGM5 cells as reference RNA to complementary DNA (cDNA) by means of the reverse transcriptase Superscript II (Invitrogen). Subsequently, the RNA was removed from the mixture by alkaline hydrolysis. In the reaction mixture a part of the dTTP was replaced by aminoallyl-dUTP (AA-dUTP) in order to render the linkage of the fluorescent dye to the cDNA possible at a later point of time.

After the purification of the reaction mixture, the cDNA of the samples and the controls were covalently labelled with the fluorescent dyes Alexa 647 and Alexa 555 and hybridized on a microarray of the SIRS-Lab company. On the microarray used, 5308 different polynucleotides with lengths of 55 to 70 base pairs were immobilised. Each of the polynucleotides represents a human gene. Additionally there were control spots for quality assurance. One microarray is divided into 28 subarrays, each of the subarrays being arranged in a grid of 15×15 spots.

The hybridization and the subsequent washing and drying, respectively, were carried out using the hybridization station HS 400 (Tecan) according to the manufacturer's instructions for 10.5 hours at 42° C. The hybridization solution used was composed of the cDNA samples, each labelled, 3.5×SSC (1×SSC comprises 150 mM sodium chloride and 15 mM sodium citrate), 0.3% sodium lauryl sulfate (v/v) 25% formamide (v/v) and each 0.8 µg µl-1 cot-1 DNA, yeast t-RNA and poly-A RNA. The subsequent washing of the microarrays was carried out at ambient temperature according to the following scheme: Rinse 90 seconds with washing buffer 1 (2×SSC, 0.03% sodium lauryl sulfate), with washing buffer 2 (1×SSC) and finally with washing buffer 3 (0.2×SSC). Subsequently, the microarrays were dried under a nitrogen flow at a pressure of 2.5 bar for more than 150 seconds at 30° C.

The hybridization signals of the processed microarrays were subsequently read by means of the GenePix 4000B (Axon) scanner and the expression ratios of the different expressed genes were determined by means of the GenePix Pro 4.0 (Axon) software.

Evaluation:

For the analysis, the average intensity of one spot was determined as median value of the corresponding spot pixel.

Correction of Systematic Errors:

Systematic errors were corrected according to the approach of Huber et al. [34]. According to this approach, the additive and the multiplicative bias in a microarray was estimated on the basis of 70% of the gene samples present. For all further computations, the signal was transformed by means of arcus sinus hyperbolicus.

For the analysis, the normalized and transformed relative ratios of the signals of the patient samples were calculated with respect to the control. This means that the calculation for the gene no. j of the patient no. n revealed the data $G_{j,n}$=arcsin h(SCy5(j,n))−arcsin h(SCy3(j,n)), wherein [SCy3(j,n), SCy5(j,n)] is the associated signal pair. When a spot could not be analysed for a patient (e.g. scanned picture is stained), the associated value was marked as "missing value".

Statistical Comparison:

For comparison the paired random student test was employed per gene. Both random samples contained the values of the patient groups of non-infectious MOF and infectious MOF, respectively. For choosing the differentially expressed genes, the associated p-value and the number of missing values were evaluated. It applied for the group of the selected genes that the associated p-vlaue was smaller than 0.05.

TABLE 3

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| N32857 | 0.00 | −2.99 | 0.20 | 1.42 | 2.78 | 1 |
| N32853 | 0.00 | −0.85 | 1.60 | 2.15 | 2.89 | 2 |
| N32495 | 0.00 | −2.38 | −0.56 | 1.37 | 0.40 | 3 |
| AI701077 | 0.01 | −0.33 | 1.46 | 0.17 | 3.08 | 4 |
| M87790 | 0.00 | 1.18 | 2.93 | 1.13 | 1.24 | 5 |
| AI559317 | 0.01 | 0.20 | 1.83 | 0.54 | 2.60 | 6 |
| N34897 | 0.00 | −2.60 | −1.05 | 1.61 | 0.54 | 7 |
| AA907084 | 0.02 | 0.53 | 1.94 | 0.49 | 2.58 | 8 |
| N45223 | 0.00 | −2.88 | −1.54 | 1.24 | 0.57 | 9 |
| H70430 | 0.03 | 0.12 | 1.42 | 0.70 | 2.73 | 10 |
| R59591 | 0.01 | −0.25 | 0.97 | 0.20 | 2.06 | 11 |
| N47688 | 0.00 | −2.47 | −1.27 | 0.94 | 0.44 | 12 |
| N52930 | 0.00 | −1.49 | −0.30 | 1.06 | 0.76 | 13 |
| XM_004256 | 0.00 | −3.10 | −1.94 | 0.62 | 1.43 | 14 |
| AJ010446 | 0.00 | −0.22 | 0.93 | 0.66 | 1.11 | 15 |
| N35225 | 0.00 | −2.81 | −1.75 | 1.21 | 0.52 | 16 |
| N50680 | 0.00 | −1.30 | −0.29 | 1.58 | 0.46 | 17 |
| BC018761 | 0.00 | 1.04 | 2.02 | 0.80 | 1.27 | 18 |
| XM_009475 | 0.00 | −2.54 | −1.58 | 0.83 | 0.91 | 19 |
| N53369 | 0.04 | −0.37 | 0.55 | 1.62 | 1.39 | 20 |
| AI420863 | 0.05 | −0.17 | 0.74 | 0.47 | 1.99 | 21 |
| N33423 | 0.05 | −0.32 | 0.58 | 1.64 | 1.51 | 22 |
| AA843281 | 0.05 | 0.27 | 1.15 | 0.54 | 1.88 | 23 |
| X64641 | 0.02 | 0.26 | 1.11 | 1.09 | 1.23 | 24 |
| N52545 | 0.00 | −1.10 | −0.28 | 1.02 | 0.55 | 25 |
| X57817 | 0.01 | 0.19 | 1.00 | 0.58 | 1.21 | 26 |
| N58236 | 0.00 | −0.68 | 0.14 | 0.85 | 0.56 | 27 |
| XM_056556 | 0.00 | −3.12 | −2.31 | 0.58 | 0.99 | 28 |
| N59170 | 0.01 | −0.22 | 0.59 | 1.35 | 0.74 | 29 |
| N58392 | 0.00 | −0.85 | −0.04 | 0.71 | 0.62 | 30 |
| N34672 | 0.02 | −0.54 | 0.26 | 1.74 | 0.39 | 31 |
| XM_015396 | 0.00 | −0.27 | 0.52 | 0.68 | 0.81 | 32 |
| X05875 | 0.01 | −2.86 | −2.09 | 0.55 | 1.15 | 33 |
| N48715 | 0.00 | −1.12 | −0.36 | 0.70 | 0.61 | 34 |
| N90140 | 0.05 | −0.44 | 0.32 | 0.29 | 1.71 | 35 |
| NM_002415 | 0.00 | −1.66 | −0.90 | 0.63 | 0.56 | 36 |
| AI890242 | 0.00 | −0.14 | 0.59 | 0.25 | 0.72 | 37 |
| AI589096 | 0.00 | −0.39 | 0.32 | 0.56 | 0.54 | 38 |
| NM_001911 | 0.04 | −2.61 | −1.91 | 0.77 | 1.44 | 39 |
| N39242 | 0.05 | −0.56 | 0.12 | 1.75 | 0.52 | 40 |
| N35493 | 0.04 | −0.45 | 0.23 | 1.69 | 0.46 | 41 |
| AI271764 | 0.00 | −0.66 | −0.02 | 0.70 | 0.62 | 42 |
| NM_006936 | 0.00 | −2.00 | −1.37 | 0.46 | 0.55 | 43 |
| NM_005225 | 0.00 | −0.90 | −0.26 | 0.58 | 0.53 | 44 |
| R98960 | 0.04 | −0.37 | 0.26 | 1.41 | 0.70 | 45 |
| NM_000714.3 | 0.00 | 0.48 | 1.11 | 0.44 | 0.88 | 46 |
| N48180 | 0.01 | −1.08 | −0.45 | 1.05 | 0.45 | 47 |
| NM_002295 | 0.02 | −3.17 | −2.56 | 0.44 | 1.09 | 48 |
| AI697365 | 0.01 | 0.62 | 1.22 | 0.82 | 0.67 | 49 |
| NM_001404 | 0.00 | −2.56 | −1.96 | 0.38 | 0.86 | 50 |
| NM_176800.1 | 0.00 | −0.31 | 0.29 | 0.51 | 0.42 | 51 |
| XM_027885 | 0.03 | −3.23 | −2.63 | 0.37 | 1.17 | 52 |
| NM_006597.3 | 0.00 | −2.42 | −1.84 | 0.50 | 0.79 | 53 |
| NM_002211 | 0.00 | −1.59 | −1.02 | 0.68 | 0.54 | 54 |
| NM_001570 | 0.00 | −0.55 | 0.03 | 0.53 | 0.49 | 55 |
| AI888606 | 0.03 | −0.16 | 0.40 | 0.44 | 1.11 | 56 |
| NM_006636.2 | 0.04 | −3.49 | −2.93 | 0.53 | 1.16 | 57 |
| AA458827 | 0.00 | 0.15 | 0.71 | 0.33 | 0.60 | 58 |
| AA398757 | 0.01 | 0.11 | 0.67 | 0.57 | 0.81 | 59 |
| NM_000814.2 | 0.00 | −0.07 | 0.49 | 0.48 | 0.75 | 60 |
| NM_000963 | 0.00 | −0.41 | 0.15 | 0.86 | 0.33 | 61 |
| AI913322 | 0.02 | −0.68 | −0.14 | 0.68 | 0.92 | 62 |
| N20922 | 0.04 | −0.72 | −0.17 | 1.27 | 0.51 | 63 |
| R49085 | 0.00 | 0.02 | 0.57 | 0.64 | 0.56 | 64 |
| N54935 | 0.01 | −0.74 | −0.19 | 0.97 | 0.38 | 65 |
| XM_027358 | 0.01 | −1.49 | −0.95 | 0.75 | 0.59 | 66 |
| NM_031200 | 0.00 | 0.11 | 0.65 | 0.57 | 0.57 | 67 |
| AA805531 | 0.00 | −0.07 | 0.47 | 0.33 | 0.53 | 68 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_000194 | 0.04 | −2.64 | −2.12 | 0.70 | 1.02 | 69 |
| AI623567 | 0.01 | 0.39 | 0.92 | 0.59 | 0.73 | 70 |
| N64495 | 0.00 | −0.49 | 0.02 | 0.63 | 0.37 | 71 |
| NM_002156 | 0.01 | −2.26 | −1.75 | 0.59 | 0.70 | 72 |
| NM_012068 | 0.00 | −1.40 | −0.89 | 0.54 | 0.40 | 73 |
| R43722 | 0.02 | −0.45 | 0.05 | 0.65 | 0.80 | 74 |
| NM_001686 | 0.03 | −2.63 | −2.13 | 0.32 | 0.93 | 75 |
| NM_002969 | 0.00 | −0.92 | −0.42 | 0.46 | 0.53 | 76 |
| NM_003295 | 0.04 | −2.72 | −2.24 | 0.45 | 0.98 | 77 |
| XM_039372 | 0.02 | −2.43 | −1.95 | 0.26 | 0.92 | 78 |
| AA731679 | 0.02 | 0.17 | 0.65 | 0.79 | 0.61 | 79 |
| AA620762 | 0.00 | −0.04 | 0.44 | 0.21 | 0.50 | 80 |
| AI499889 | 0.01 | −0.01 | 0.47 | 0.67 | 0.64 | 81 |
| N33530 | 0.00 | −0.30 | 0.18 | 0.70 | 0.31 | 82 |
| NM_002033 | 0.00 | −1.92 | −1.44 | 0.39 | 0.63 | 83 |
| AA436651 | 0.00 | −0.26 | 0.21 | 0.54 | 0.26 | 84 |
| NM_001540 | 0.00 | −1.42 | −0.95 | 0.42 | 0.54 | 85 |
| NM_004257 | 0.00 | −0.85 | −0.38 | 0.33 | 0.25 | 86 |
| NM_014280.1 | 0.00 | −1.45 | −0.98 | 0.58 | 0.47 | 87 |
| NM_000930.2 | 0.00 | −1.30 | −0.83 | 0.64 | 0.51 | 88 |
| XM_002101 | 0.00 | −0.63 | −0.17 | 0.63 | 0.27 | 89 |
| AI733269 | 0.00 | −0.18 | 0.29 | 0.45 | 0.36 | 90 |
| NM_001168 | 0.02 | −2.14 | −1.67 | 0.61 | 0.77 | 91 |
| XM_052636 | 0.00 | −1.51 | −1.04 | 0.35 | 0.48 | 92 |
| AI689318 | 0.00 | −1.00 | −0.54 | 0.55 | 0.46 | 93 |
| NM_001212 | 0.01 | −1.65 | −1.19 | 0.56 | 0.64 | 94 |
| R37251 | 0.00 | 0.61 | 1.06 | 0.39 | 0.63 | 95 |
| NM_001166 | 0.00 | −0.76 | −0.31 | 0.53 | 0.41 | 96 |
| XM_056798 | 0.01 | −1.34 | −0.89 | 0.66 | 0.51 | 97 |
| NM_005052 | 0.01 | 0.41 | 0.86 | 0.37 | 0.67 | 98 |
| NM_003379 | 0.00 | −1.45 | −1.00 | 0.41 | 0.51 | 99 |
| XM_048068 | 0.00 | −0.37 | 0.08 | 0.43 | 0.42 | 100 |
| NM_000577 | 0.01 | 0.45 | 0.90 | 0.32 | 0.67 | 101 |
| NM_001101 | 0.00 | −0.69 | −0.25 | 0.43 | 0.58 | 102 |
| D31890 | 0.01 | −1.79 | −1.36 | 0.56 | 0.55 | 103 |
| N49976 | 0.03 | −0.26 | 0.17 | 0.90 | 0.50 | 104 |
| XM_008679 | 0.01 | −0.85 | −0.41 | 0.57 | 0.56 | 105 |
| N33187 | 0.01 | −0.06 | 0.38 | 0.52 | 0.54 | 106 |
| R42782 | 0.00 | −0.09 | 0.34 | 0.36 | 0.45 | 107 |
| N49751 | 0.01 | 0.71 | 1.14 | 0.48 | 0.64 | 108 |
| AI910456 | 0.04 | −1.12 | −0.69 | 0.73 | 0.75 | 109 |
| NM_001569 | 0.00 | −1.10 | −0.67 | 0.38 | 0.46 | 110 |
| H90322 | 0.00 | 0.05 | 0.48 | 0.27 | 0.51 | 111 |
| AI926659 | 0.00 | 0.05 | 0.48 | 0.37 | 0.44 | 112 |
| XM_047499 | 0.01 | −1.29 | −0.86 | 0.46 | 0.67 | 113 |
| AA437224 | 0.00 | −0.71 | −0.28 | 0.46 | 0.24 | 114 |
| NM_021798 | 0.00 | −0.32 | 0.11 | 0.44 | 0.36 | 115 |
| NM_000584 | 0.02 | −1.82 | −1.40 | 0.61 | 0.64 | 116 |
| AA452122 | 0.00 | −0.40 | 0.02 | 0.60 | 0.41 | 117 |
| NM_002189 | 0.01 | 0.10 | 0.52 | 0.48 | 0.57 | 118 |
| AA001367 | 0.00 | −0.13 | 0.29 | 0.37 | 0.57 | 119 |
| AI129679 | 0.00 | −1.27 | −0.85 | 0.31 | 0.37 | 120 |
| D26599 | 0.01 | −1.90 | −1.48 | 0.50 | 0.58 | 121 |
| NM_170665.2 | 0.00 | −1.19 | −0.78 | 0.49 | 0.45 | 122 |
| NM_006419 | 0.00 | −0.16 | 0.25 | 0.39 | 0.51 | 123 |
| W85706 | 0.00 | −1.07 | −0.66 | 0.30 | 0.37 | 124 |
| AA897528 | 0.00 | −0.50 | −0.09 | 0.65 | 0.30 | 125 |
| NM_003358 | 0.04 | 0.56 | 0.97 | 0.50 | 0.82 | 126 |
| N35251 | 0.00 | −0.18 | 0.22 | 0.52 | 0.41 | 127 |
| NM_004863 | 0.00 | −0.63 | −0.22 | 0.37 | 0.48 | 128 |
| NM_001950 | 0.00 | −0.82 | −0.41 | 0.40 | 0.33 | 129 |
| NM_006260 | 0.03 | −0.63 | −0.22 | 0.61 | 0.67 | 130 |
| NM_170708 | 0.03 | −1.52 | −1.12 | 0.54 | 0.63 | 131 |
| N63024 | 0.01 | 0.64 | 1.04 | 0.43 | 0.56 | 132 |
| NM_017595 | 0.00 | −0.85 | −0.45 | 0.36 | 0.33 | 133 |
| AI364529 | 0.02 | −0.97 | −0.57 | 0.59 | 0.59 | 134 |
| NM_013432 | 0.00 | −0.30 | 0.10 | 0.31 | 0.28 | 135 |
| NM_006736.2 | 0.00 | −0.56 | −0.16 | 0.24 | 0.37 | 136 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| NM_002128 | 0.02 | −1.84 | −1.44 | 0.40 | 0.69 | 137 |
| AA441793 | 0.00 | −0.70 | −0.31 | 0.45 | 0.33 | 138 |
| N76019 | 0.00 | −0.27 | 0.13 | 0.35 | 0.30 | 139 |
| XM_048665 | 0.00 | −0.28 | 0.11 | 0.38 | 0.35 | 140 |
| NM_003467 | 0.01 | −1.80 | −1.41 | 0.32 | 0.62 | 141 |
| N59330 | 0.01 | −0.21 | 0.19 | 0.56 | 0.50 | 142 |
| NM_004672 | 0.00 | −0.08 | 0.32 | 0.44 | 0.26 | 143 |
| AA426021 | 0.01 | 0.06 | 0.45 | 0.28 | 0.61 | 144 |
| XM_008608 | 0.00 | −0.60 | −0.21 | 0.54 | 0.34 | 145 |
| H44908 | 0.00 | −0.55 | −0.16 | 0.42 | 0.33 | 146 |
| AA699412 | 0.00 | −0.47 | −0.08 | 0.48 | 0.35 | 147 |
| AI572080 | 0.01 | 0.28 | 0.67 | 0.41 | 0.52 | 148 |
| NM_012072 | 0.02 | −1.86 | −1.47 | 0.47 | 0.63 | 149 |
| XM_035638 | 0.04 | −1.96 | −1.57 | 0.40 | 0.80 | 150 |
| BC001604 | 0.00 | −1.13 | −0.74 | 0.40 | 0.33 | 151 |
| AA481282 | 0.00 | −0.11 | 0.27 | 0.54 | 0.40 | 152 |
| NM_003376 | 0.01 | −1.17 | −0.78 | 0.54 | 0.42 | 153 |
| H11661 | 0.00 | −0.07 | 0.32 | 0.25 | 0.37 | 154 |
| AI435179 | 0.01 | −0.08 | 0.30 | 0.68 | 0.37 | 155 |
| XM_006800 | 0.01 | 0.19 | 0.57 | 0.38 | 0.55 | 156 |
| NM_000397.2 | 0.00 | −0.56 | −0.17 | 0.37 | 0.28 | 157 |
| AA424023 | 0.02 | 0.01 | 0.39 | 0.43 | 0.63 | 158 |
| XM_012949 | 0.02 | −1.81 | −1.43 | 0.45 | 0.64 | 159 |
| W84866 | 0.00 | 0.14 | 0.52 | 0.44 | 0.45 | 160 |
| N62672 | 0.01 | −0.21 | 0.17 | 0.60 | 0.44 | 161 |
| NM_001530 | 0.01 | −0.16 | 0.21 | 0.25 | 0.62 | 162 |
| NM_002157.1 | 0.03 | −2.21 | −1.83 | 0.43 | 0.71 | 163 |
| NM_003258 | 0.02 | −1.80 | −1.43 | 0.68 | 0.46 | 164 |
| AI863135 | 0.04 | 0.87 | 1.25 | 0.40 | 0.76 | 165 |
| NM_004083 | 0.01 | −0.95 | −0.58 | 0.46 | 0.47 | 166 |
| H06194 | 0.00 | −0.92 | −0.54 | 0.45 | 0.30 | 167 |
| XM_047570 | 0.03 | −1.61 | −1.24 | 0.41 | 0.68 | 168 |
| D26598 | 0.01 | −1.23 | −0.86 | 0.27 | 0.57 | 169 |
| R44955 | 0.01 | −0.08 | 0.29 | 0.55 | 0.49 | 170 |
| NM_012297 | 0.02 | −1.60 | −1.22 | 0.48 | 0.59 | 171 |
| T84080 | 0.02 | 0.13 | 0.49 | 0.57 | 0.52 | 172 |
| H52810 | 0.00 | 0.13 | 0.50 | 0.33 | 0.44 | 173 |
| XM_055188 | 0.04 | 0.94 | 1.30 | 0.36 | 0.75 | 174 |
| AI184987 | 0.01 | 0.19 | 0.56 | 0.51 | 0.50 | 175 |
| AI733177 | 0.02 | 0.54 | 0.90 | 0.41 | 0.63 | 176 |
| NM_006016 | 0.02 | −1.15 | −0.78 | 0.44 | 0.60 | 177 |
| XM_006867 | 0.02 | 0.09 | 0.46 | 0.33 | 0.62 | 178 |
| NM_004475.1 | 0.02 | 0.95 | 1.32 | 0.40 | 0.60 | 179 |
| AA485242 | 0.03 | 0.34 | 0.70 | 0.49 | 0.62 | 180 |
| NM_003300 | 0.01 | −1.49 | −1.13 | 0.31 | 0.54 | 181 |
| NM_032957 | 0.00 | −0.88 | −0.52 | 0.32 | 0.39 | 182 |
| XM_033862 | 0.00 | −0.01 | 0.35 | 0.29 | 0.36 | 183 |
| W80385 | 0.01 | 0.10 | 0.46 | 0.36 | 0.52 | 184 |
| H99099 | 0.01 | −0.04 | 0.32 | 0.37 | 0.52 | 185 |
| N67859 | 0.00 | −0.77 | −0.41 | 0.34 | 0.39 | 186 |
| NM_001013 | 0.04 | −1.88 | −1.52 | 0.44 | 0.68 | 187 |
| NM_006641 | 0.02 | −0.36 | 0.00 | 0.69 | 0.35 | 188 |
| N70546 | 0.00 | −0.11 | 0.25 | 0.38 | 0.40 | 189 |
| XM_015278 | 0.00 | −0.36 | −0.01 | 0.33 | 0.42 | 190 |
| AI932670 | 0.00 | −0.15 | 0.20 | 0.36 | 0.43 | 191 |
| NM_175617 | 0.00 | −0.11 | 0.25 | 0.29 | 0.26 | 192 |
| NM_004377.2 | 0.02 | −0.88 | −0.53 | 0.52 | 0.50 | 193 |
| NM_003153 | 0.00 | −0.39 | −0.04 | 0.30 | 0.48 | 194 |
| AI910804 | 0.03 | −0.65 | −0.30 | 0.51 | 0.57 | 195 |
| AI221860 | 0.00 | −0.30 | 0.05 | 0.17 | 0.43 | 196 |
| AI866414 | 0.00 | −0.37 | −0.02 | 0.33 | 0.27 | 197 |
| BC020968 | 0.03 | −1.77 | −1.42 | 0.36 | 0.65 | 198 |
| AA484213 | 0.05 | −0.49 | −0.14 | 0.90 | 0.27 | 199 |
| XM_003593 | 0.00 | −0.52 | −0.17 | 0.44 | 0.27 | 200 |
| XM_008738 | 0.02 | −1.46 | −1.11 | 0.54 | 0.49 | 201 |
| NM_032964 | 0.00 | −0.48 | −0.13 | 0.41 | 0.20 | 202 |
| NM_001455 | 0.00 | 0.26 | 0.61 | 0.42 | 0.41 | 203 |
| NM_002994 | 0.00 | −0.61 | −0.26 | 0.35 | 0.43 | 204 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
| | | Group of patients with non-infectious MOF | Group of patients with infectious MOF | Group of patients with non-infectious MOF | Group of patients with infectious MOF | |
|---|---|---|---|---|---|---|
| NM_004222 | 0.00 | −1.44 | −1.10 | 0.30 | 0.45 | 205 |
| H48923 | 0.00 | −0.59 | −0.25 | 0.35 | 0.39 | 206 |
| T47430 | 0.05 | 0.41 | 0.75 | 0.38 | 0.71 | 207 |
| NM_032963 | 0.00 | −0.45 | −0.11 | 0.52 | 0.22 | 208 |
| XM_045933 | 0.00 | 0.22 | 0.56 | 0.23 | 0.41 | 209 |
| T99746 | 0.03 | 0.26 | 0.60 | 0.49 | 0.52 | 210 |
| XM_012039 | 0.01 | −1.44 | −1.10 | 0.44 | 0.43 | 211 |
| NM_004740 | 0.00 | −0.46 | −0.12 | 0.29 | 0.24 | 212 |
| NM_001681.2 | 0.05 | −1.39 | −0.05 | 0.61 | 0.60 | 213 |
| AI027259 | 0.00 | −0.40 | −0.06 | 0.49 | 0.28 | 214 |
| AA431552 | 0.00 | −0.63 | −0.30 | 0.41 | 0.32 | 215 |
| NM_000029 | 0.00 | 0.30 | 0.63 | 0.32 | 0.42 | 216 |
| XM_041847 | 0.05 | −1.02 | −0.68 | 0.69 | 0.51 | 217 |
| NM_005920 | 0.00 | −0.90 | −0.56 | 0.28 | 0.33 | 218 |
| NM_002394 | 0.01 | −1.03 | −0.69 | 0.49 | 0.39 | 219 |
| AI093704 | 0.01 | −0.32 | 0.02 | 0.35 | 0.47 | 220 |
| XM_043359 | 0.01 | 0.21 | 0.55 | 0.36 | 0.51 | 221 |
| H48445 | 0.01 | 0.28 | 0.61 | 0.38 | 0.53 | 222 |
| XM_015815 | 0.02 | −1.13 | −0.80 | 0.52 | 0.50 | 223 |
| NM_001774 | 0.00 | −0.07 | 0.27 | 0.31 | 0.42 | 224 |
| AI937053 | 0.00 | −0.42 | −0.09 | 0.39 | 0.26 | 225 |
| AA493719 | 0.01 | −0.61 | −0.28 | 0.52 | 0.35 | 226 |
| NM_002996 | 0.01 | 0.19 | 0.51 | 0.33 | 0.44 | 227 |
| AI025039 | 0.01 | 0.16 | 0.49 | 0.31 | 0.47 | 228 |
| NM_139049 | 0.02 | −0.52 | −0.19 | 0.60 | 0.34 | 229 |
| NM_006238.2 | 0.00 | −0.29 | 0.04 | 0.21 | 0.26 | 230 |
| XM_031456 | 0.00 | −0.67 | −0.35 | 0.30 | 0.30 | 231 |
| AA455096 | 0.00 | −0.29 | 0.03 | 0.29 | 0.32 | 232 |
| XM_047675 | 0.03 | 0.36 | 0.68 | 0.26 | 0.65 | 233 |
| AI809252 | 0.00 | −0.14 | 0.18 | 0.36 | 0.34 | 234 |
| NM_139047 | 0.00 | −0.45 | −0.13 | 0.47 | 0.31 | 235 |
| AI760793 | 0.01 | −0.47 | −0.15 | 0.47 | 0.33 | 236 |
| NM_000204 | 0.00 | −0.03 | 0.29 | 0.25 | 0.40 | 237 |
| AI860121 | 0.01 | 0.55 | 0.87 | 0.37 | 0.48 | 238 |
| H50222 | 0.00 | −0.13 | 0.19 | 0.19 | 0.34 | 239 |
| XM_041101 | 0.02 | −1.06 | −0.74 | 0.34 | 0.56 | 240 |
| XM_035854 | 0.01 | 0.09 | 0.41 | 0.47 | 0.44 | 241 |
| AA043903 | 0.01 | −0.73 | −0.41 | 0.52 | 0.31 | 242 |
| R40406 | 0.03 | −0.89 | −0.58 | 0.48 | 0.52 | 243 |
| N98510 | 0.04 | −1.22 | −0.90 | 0.51 | 0.56 | 244 |
| H05449 | 0.03 | −0.15 | 0.16 | 0.52 | 0.50 | 245 |
| AI567338 | 0.01 | −0.11 | 0.20 | 0.43 | 0.39 | 246 |
| NM_000308.1 | 0.00 | −0.19 | 0.13 | 0.29 | 0.42 | 247 |
| R40880 | 0.00 | −0.21 | 0.11 | 0.40 | 0.34 | 248 |
| H52284 | 0.00 | −0.26 | 0.05 | 0.41 | 0.27 | 249 |
| NM_030662 | 0.00 | −0.47 | −0.16 | 0.22 | 0.27 | 250 |
| NM_032965 | 0.02 | 0.52 | 0.83 | 0.41 | 0.47 | 251 |
| NM_004322 | 0.00 | −0.34 | −0.03 | 0.32 | 0.27 | 252 |
| XM_002762 | 0.00 | −0.52 | −0.21 | 0.22 | 0.25 | 253 |
| AI679230 | 0.00 | −0.40 | −0.09 | 0.43 | 0.33 | 254 |
| AI368670 | 0.00 | −0.23 | 0.08 | 0.30 | 0.31 | 255 |
| NM_006415 | 0.01 | −0.71 | −0.40 | 0.45 | 0.33 | 256 |
| NM_004379 | 0.00 | −0.54 | −0.23 | 0.24 | 0.24 | 257 |
| NM_002974 | 0.02 | 0.02 | 0.33 | 0.49 | 0.38 | 258 |
| AI914729 | 0.02 | −0.11 | 0.20 | 0.51 | 0.40 | 259 |
| NM_032989 | 0.00 | −0.17 | 0.14 | 0.23 | 0.28 | 260 |
| AI799645 | 0.04 | 0.14 | 0.45 | 0.39 | 0.61 | 261 |
| AA436553 | 0.01 | −0.33 | −0.03 | 0.59 | 0.24 | 262 |
| NM_033015 | 0.00 | −0.37 | −0.06 | 0.32 | 0.25 | 263 |
| XM_002224 | 0.01 | −0.26 | 0.04 | 0.57 | 0.28 | 264 |
| AI708030 | 0.00 | 0.11 | 0.41 | 0.37 | 0.32 | 265 |
| AI041544 | 0.00 | −0.28 | 0.02 | 0.28 | 0.27 | 266 |
| NM_005801 | 0.03 | −1.39 | −1.09 | 0.36 | 0.54 | 267 |
| NM_022559 | 0.00 | −0.63 | −0.33 | 0.42 | 0.24 | 268 |
| XM_043864 | 0.00 | −0.40 | −0.10 | 0.32 | 0.31 | 269 |
| NM_003840 | 0.01 | −0.42 | −0.12 | 0.52 | 0.25 | 270 |
| AI565083 | 0.00 | −0.28 | 0.02 | 0.32 | 0.24 | 271 |
| R91168 | 0.01 | 0.15 | 0.45 | 0.36 | 0.40 | 272 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AI799787 | 0.01 | 0.12 | 0.41 | 0.34 | 0.38 | 273 |
| AI652564 | 0.00 | −0.91 | −0.61 | 0.31 | 0.30 | 274 |
| H05310 | 0.00 | 0.02 | 0.32 | 0.30 | 0.29 | 275 |
| AA708806 | 0.00 | −0.22 | 0.08 | 0.24 | 0.26 | 276 |
| H74205 | 0.03 | 0.07 | 0.37 | 0.42 | 0.49 | 277 |
| NM_000061 | 0.03 | −1.59 | −1.30 | 0.40 | 0.53 | 278 |
| NM_003110.3 | 0.00 | −0.29 | 0.00 | 0.38 | 0.27 | 279 |
| AA625887 | 0.00 | −0.30 | −0.01 | 0.22 | 0.23 | 280 |
| H41124 | 0.03 | −0.37 | −0.08 | 0.39 | 0.48 | 281 |
| AI769514 | 0.02 | −0.58 | −0.28 | 0.56 | 0.35 | 282 |
| XM_036107 | 0.03 | −0.27 | 0.02 | 0.27 | 0.53 | 283 |
| R52679 | 0.01 | −1.03 | −0.74 | 0.36 | 0.35 | 284 |
| AI217811 | 0.04 | 0.02 | 0.31 | 0.31 | 0.59 | 285 |
| NM_004168 | 0.02 | −0.63 | −0.34 | 0.42 | 0.44 | 286 |
| AI933607 | 0.03 | −0.24 | 0.05 | 0.32 | 0.55 | 287 |
| NM_007052.3 | 0.03 | −0.24 | 0.05 | 0.61 | 0.29 | 288 |
| AI799137 | 0.02 | −0.42 | −0.12 | 0.52 | 0.37 | 289 |
| NM_002720 | 0.00 | −0.64 | −0.35 | 0.28 | 0.34 | 290 |
| R26635 | 0.04 | −0.16 | 0.13 | 0.32 | 0.57 | 291 |
| AI625594 | 0.00 | −0.01 | 0.28 | 0.29 | 0.31 | 292 |
| NM_001562 | 0.00 | −0.42 | −0.13 | 0.22 | 0.27 | 293 |
| W93717 | 0.05 | 0.11 | 0.40 | 0.64 | 0.40 | 294 |
| NM_002521.1 | 0.01 | −0.10 | 0.19 | 0.44 | 0.29 | 295 |
| R42543 | 0.05 | 0.26 | 0.55 | 0.45 | 0.54 | 296 |
| AI302949 | 0.00 | −0.13 | 0.16 | 0.21 | 0.23 | 297 |
| H54279 | 0.00 | −0.01 | 0.27 | 0.29 | 0.32 | 298 |
| AI219513 | 0.00 | −0.47 | −0.19 | 0.41 | 0.27 | 299 |
| N68173 | 0.00 | −0.11 | 0.18 | 0.26 | 0.38 | 300 |
| AA496235 | 0.00 | −0.38 | −0.09 | 0.41 | 0.28 | 301 |
| AI742529 | 0.03 | 0.39 | 0.67 | 0.33 | 0.51 | 302 |
| H79534 | 0.01 | −0.50 | −0.21 | 0.47 | 0.32 | 303 |
| AA002267 | 0.03 | −0.04 | 0.25 | 0.36 | 0.47 | 304 |
| H52638 | 0.00 | −0.38 | −0.10 | 0.40 | 0.28 | 305 |
| N70324 | 0.01 | 0.07 | 0.35 | 0.47 | 0.33 | 306 |
| NM_003805 | 0.02 | −0.83 | −0.55 | 0.47 | 0.36 | 307 |
| N59766 | 0.03 | −0.04 | 0.24 | 0.41 | 0.43 | 308 |
| XM_034770 | 0.04 | −1.26 | −0.98 | 0.44 | 0.45 | 309 |
| AI538438 | 0.01 | 0.06 | 0.34 | 0.43 | 0.31 | 310 |
| AI250800 | 0.00 | 0.05 | 0.32 | 0.23 | 0.29 | 311 |
| AA845475 | 0.00 | −0.24 | 0.04 | 0.39 | 0.25 | 312 |
| AI700169 | 0.00 | −0.23 | 0.05 | 0.33 | 0.30 | 313 |
| NM_003639) | 0.00 | −0.37 | −0.09 | 0.26 | 0.31 | 314 |
| AI125864 | 0.03 | −0.27 | 0.01 | 0.60 | 0.24 | 315 |
| NM_000757 | 0.03 | 0.12 | 0.40 | 0.38 | 0.48 | 316 |
| NM_006216 | 0.03 | −0.12 | 0.16 | 0.45 | 0.42 | 317 |
| AI077481 | 0.04 | 0.21 | 0.49 | 0.41 | 0.48 | 318 |
| AI149647 | 0.03 | −0.13 | 0.15 | 0.43 | 0.46 | 319 |
| XM_030906 | 0.01 | 0.18 | 0.45 | 0.28 | 0.39 | 320 |
| NM_004834 | 0.00 | −0.68 | −0.41 | 0.27 | 0.35 | 321 |
| XM_031287 | 0.01 | 0.11 | 0.38 | 0.27 | 0.41 | 322 |
| AI923251 | 0.00 | −0.25 | 0.02 | 0.20 | 0.24 | 323 |
| AI203697 | 0.00 | −0.22 | 0.05 | 0.31 | 0.18 | 324 |
| AA621192 | 0.02 | 0.04 | 0.31 | 0.34 | 0.45 | 325 |
| XM_008450 | 0.02 | −0.24 | 0.03 | 0.51 | 0.29 | 326 |
| AI540674 | 0.00 | −0.76 | −0.49 | 0.25 | 0.34 | 327 |
| AA514237 | 0.03 | 0.35 | 0.62 | 0.31 | 0.47 | 328 |
| AI348271 | 0.01 | −0.11 | 0.16 | 0.45 | 0.26 | 329 |
| NM_000684.1 | 0.02 | 0.41 | 0.68 | 0.29 | 0.44 | 330 |
| NM_001951 | 0.03 | −0.67 | −0.40 | 0.50 | 0.40 | 331 |
| N55249 | 0.01 | −0.42 | −0.15 | 0.45 | 0.31 | 332 |
| AI150732 | 0.01 | −0.20 | 0.07 | 0.34 | 0.34 | 333 |
| AI147315 | 0.03 | 0.35 | 0.62 | 0.38 | 0.45 | 334 |
| NM_003010 | 0.00 | −0.46 | −0.20 | 0.34 | 0.25 | 335 |
| AA460460 | 0.01 | −0.22 | 0.05 | 0.47 | 0.28 | 336 |
| AI651337 | 0.01 | −0.49 | −0.22 | 0.41 | 0.31 | 337 |
| AA971087 | 0.01 | −0.19 | 0.08 | 0.42 | 0.25 | 338 |
| NM_003811 | 0.03 | −1.09 | −0.82 | 0.50 | 0.37 | 339 |
| XM_053519 | 0.01 | −0.30 | −0.04 | 0.26 | 0.39 | 340 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| NM_001609.1 | 0.00 | −0.24 | 0.03 | 0.29 | 0.29 | 341 |
| AA463423 | 0.00 | −0.17 | 0.09 | 0.22 | 0.35 | 342 |
| AA648848 | 0.02 | 0.04 | 0.30 | 0.35 | 0.42 | 343 |
| AI141692 | 0.05 | −0.12 | 0.14 | 0.67 | 0.22 | 344 |
| R79239 | 0.04 | 0.06 | 0.33 | 0.50 | 0.42 | 345 |
| AI298171 | 0.00 | −0.28 | −0.01 | 0.17 | 0.21 | 346 |
| H17432 | 0.03 | −0.29 | −0.03 | 0.57 | 0.23 | 347 |
| NM_004635 | 0.05 | −1.36 | −1.10 | 0.31 | 0.51 | 348 |
| NM_005409 | 0.02 | 0.14 | 0.40 | 0.20 | 0.50 | 349 |
| AI452845 | 0.03 | 0.23 | 0.49 | 0.37 | 0.43 | 350 |
| AI222914 | 0.00 | −0.03 | 0.23 | 0.29 | 0.24 | 351 |
| AI885492 | 0.00 | −0.06 | 0.20 | 0.34 | 0.20 | 352 |
| NM_002953 | 0.01 | −0.61 | −0.35 | 0.24 | 0.41 | 353 |
| AI201175 | 0.01 | 0.25 | 0.51 | 0.30 | 0.33 | 354 |
| NM_001735 | 0.02 | −0.45 | −0.20 | 0.47 | 0.29 | 355 |
| D78151 | 0.02 | −0.70 | −0.44 | 0.42 | 0.34 | 356 |
| NM_006712 | 0.00 | −0.20 | 0.06 | 0.36 | 0.24 | 357 |
| AF004429 | 0.00 | −0.63 | −0.37 | 0.29 | 0.29 | 358 |
| NM_031409 | 0.03 | 0.19 | 0.44 | 0.32 | 0.45 | 359 |
| AI742287 | 0.01 | −0.30 | −0.04 | 0.41 | 0.27 | 360 |
| BC015542 | 0.02 | −0.42 | −0.16 | 0.34 | 0.42 | 361 |
| AI685923 | 0.00 | −0.43 | −0.18 | 0.32 | 0.22 | 362 |
| NM_002218.1 | 0.01 | −0.55 | −0.29 | 0.34 | 0.28 | 363 |
| XM_003913 | 0.00 | −0.05 | 0.20 | 0.29 | 0.29 | 364 |
| N53480 | 0.02 | −0.64 | −0.39 | 0.40 | 0.38 | 365 |
| XM_048511 | 0.00 | −0.35 | −0.10 | 0.37 | 0.25 | 366 |
| R06710 | 0.02 | 0.05 | 0.30 | 0.39 | 0.35 | 367 |
| AI694720 | 0.01 | 0.29 | 0.54 | 0.28 | 0.34 | 368 |
| AI910988 | 0.00 | 0.07 | 0.32 | 0.23 | 0.33 | 369 |
| AA411624 | 0.02 | −0.52 | −0.27 | 0.33 | 0.38 | 370 |
| BC024270 | 0.00 | −0.43 | −0.18 | 0.32 | 0.27 | 371 |
| T90460 | 0.01 | −0.39 | −0.14 | 0.48 | 0.17 | 372 |
| NM_004850 | 0.02 | −0.92 | −0.67 | 0.41 | 0.32 | 373 |
| AA044390 | 0.03 | −0.01 | 0.24 | 0.26 | 0.45 | 374 |
| NM_005347.2 | 0.00 | −0.26 | −0.01 | 0.21 | 0.23 | 375 |
| XM_027216 | 0.03 | −0.68 | −0.43 | 0.42 | 0.39 | 376 |
| H53259 | 0.04 | 0.45 | 0.70 | 0.35 | 0.45 | 377 |
| R26717 | 0.02 | −0.02 | 0.22 | 0.40 | 0.35 | 378 |
| AI912970 | 0.02 | 0.19 | 0.44 | 0.36 | 0.35 | 379 |
| XM_001687 | 0.04 | −0.91 | −0.66 | 0.44 | 0.40 | 380 |
| NM_000565 | 0.04 | −0.67 | −0.43 | 0.27 | 0.50 | 381 |
| AI374990 | 0.01 | −0.14 | 0.10 | 0.31 | 0.35 | 382 |
| N22563 | 0.02 | 0.12 | 0.37 | 0.33 | 0.39 | 383 |
| AI764969 | 0.03 | −0.18 | 0.07 | 0.53 | 0.25 | 384 |
| AA417950 | 0.02 | −0.34 | −0.09 | 0.48 | 0.26 | 385 |
| H15431 | 0.03 | −0.39 | −0.14 | 0.51 | 0.30 | 386 |
| AI147997 | 0.02 | 0.11 | 0.35 | 0.24 | 0.45 | 387 |
| AI378142 | 0.03 | −0.10 | 0.14 | 0.25 | 0.42 | 388 |
| AA528101 | 0.00 | −0.43 | −0.19 | 0.32 | 0.21 | 389 |
| T83761 | 0.04 | −0.41 | −0.16 | 0.36 | 0.46 | 390 |
| XM_046674 | 0.04 | −0.80 | −0.56 | 0.59 | 0.21 | 391 |
| AI925556 | 0.00 | −0.53 | −0.29 | 0.24 | 0.21 | 392 |
| N50785 | 0.03 | 0.25 | 0.49 | 0.29 | 0.43 | 393 |
| AI739085 | 0.04 | −0.41 | −0.17 | 0.41 | 0.39 | 394 |
| AA885052 | 0.02 | −0.13 | 0.11 | 0.42 | 0.28 | 395 |
| R45218 | 0.01 | 0.17 | 0.41 | 0.25 | 0.37 | 396 |
| N71365 | 0.00 | −0.39 | −0.15 | 0.22 | 0.33 | 397 |
| AI590053 | 0.00 | −0.38 | −0.14 | 0.19 | 0.16 | 398 |
| NM_013229 | 0.00 | 0.02 | 0.26 | 0.22 | 0.26 | 399 |
| NM_001196 | 0.02 | −0.53 | −0.30 | 0.27 | 0.39 | 400 |
| R94509 | 0.01 | 0.07 | 0.31 | 0.29 | 0.29 | 401 |
| AA282936 | 0.02 | 0.16 | 0.39 | 0.41 | 0.33 | 402 |
| NM_003824 | 0.01 | −0.74 | −0.50 | 0.26 | 0.37 | 403 |
| T65296 | 0.01 | 0.00 | 0.23 | 0.23 | 0.34 | 404 |
| AI583064 | 0.03 | 0.01 | 0.24 | 0.28 | 0.42 | 405 |
| R94626 | 0.01 | −0.25 | −0.01 | 0.25 | 0.35 | 406 |
| AI216612 | 0.03 | −0.20 | 0.03 | 0.42 | 0.35 | 407 |
| NM_015318.1 | 0.01 | −0.12 | 0.11 | 0.32 | 0.25 | 408 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AA426397 | 0.02 | −0.37 | −0.14 | 0.33 | 0.34 | 409 |
| H78362 | 0.01 | −0.53 | −0.30 | 0.31 | 0.27 | 410 |
| AA878269 | 0.02 | −0.28 | −0.05 | 0.32 | 0.34 | 411 |
| NM_017778 | 0.01 | −0.17 | 0.06 | 0.39 | 0.26 | 412 |
| AI709236 | 0.00 | −0.24 | −0.01 | 0.21 | 0.28 | 413 |
| AA465175 | 0.01 | −0.11 | 0.12 | 0.32 | 0.27 | 414 |
| AI798573 | 0.00 | −0.34 | −0.12 | 0.18 | 0.21 | 415 |
| NM_139070 | 0.02 | −0.87 | −0.64 | 0.41 | 0.27 | 416 |
| XM_049749 | 0.04 | −0.18 | 0.05 | 0.50 | 0.28 | 417 |
| AI864931 | 0.01 | 0.09 | 0.31 | 0.24 | 0.31 | 418 |
| NM_021975 | 0.00 | −0.63 | −0.41 | 0.29 | 0.22 | 419 |
| R60931 | 0.03 | 0.16 | 0.39 | 0.35 | 0.35 | 420 |
| XM_037260 | 0.00 | −0.38 | −0.15 | 0.18 | 0.26 | 421 |
| R36650 | 0.00 | −0.40 | −0.17 | 0.23 | 0.25 | 422 |
| AA621075 | 0.00 | −0.31 | −0.09 | 0.24 | 0.28 | 423 |
| AI018273 | 0.04 | −0.23 | 0.00 | 0.45 | 0.31 | 424 |
| AI701905 | 0.00 | −0.24 | −0.01 | 0.22 | 0.24 | 425 |
| XM_054686 | 0.02 | −0.55 | −0.33 | 0.30 | 0.31 | 426 |
| NM_139276 | 0.02 | −0.09 | 0.14 | 0.25 | 0.38 | 427 |
| AI418064 | 0.01 | −0.23 | −0.01 | 0.32 | 0.24 | 428 |
| NM_002503 | 0.03 | −0.50 | −0.28 | 0.40 | 0.32 | 429 |
| AI923559 | 0.02 | −0.37 | −0.15 | 0.35 | 0.33 | 430 |
| NM_004295 | 0.04 | −0.66 | −0.44 | 0.40 | 0.37 | 431 |
| AA425105 | 0.03 | −0.19 | 0.04 | 0.43 | 0.29 | 432 |
| NM_002997 | 0.02 | 0.01 | 0.24 | 0.37 | 0.28 | 433 |
| NM_024013 | 0.00 | 0.04 | 0.27 | 0.28 | 0.23 | 434 |
| AA856755 | 0.02 | −0.40 | −0.18 | 0.34 | 0.34 | 435 |
| AI371339 | 0.00 | −0.28 | −0.06 | 0.24 | 0.22 | 436 |
| AA453528 | 0.04 | −0.30 | −0.08 | 0.50 | 0.27 | 437 |
| AI214646 | 0.04 | −0.27 | −0.05 | 0.24 | 0.43 | 438 |
| NM_006724 | 0.01 | −0.45 | −0.22 | 0.32 | 0.24 | 439 |
| AI925740 | 0.02 | 0.02 | 0.24 | 0.42 | 0.25 | 440 |
| H81378 | 0.00 | −0.16 | 0.06 | 0.32 | 0.19 | 441 |
| H82860 | 0.03 | 0.01 | 0.23 | 0.25 | 0.41 | 442 |
| BC032713 | 0.02 | 0.39 | 0.61 | 0.22 | 0.37 | 443 |
| H10036 | 0.05 | −0.08 | 0.13 | 0.42 | 0.35 | 444 |
| AI707917 | 0.00 | −0.34 | −0.12 | 0.18 | 0.20 | 445 |
| AA676928 | 0.05 | −0.04 | 0.18 | 0.36 | 0.40 | 446 |
| AI057616 | 0.00 | −0.03 | 0.19 | 0.19 | 0.30 | 447 |
| NM_003080 | 0.01 | −0.03 | 0.18 | 0.29 | 0.25 | 448 |
| AI685198 | 0.00 | −0.41 | −0.20 | 0.19 | 0.23 | 449 |
| AA436683 | 0.02 | −0.16 | 0.05 | 0.34 | 0.29 | 450 |
| R39456 | 0.00 | −0.34 | −0.13 | 0.17 | 0.23 | 451 |
| NM_004050 | 0.03 | −0.23 | −0.02 | 0.38 | 0.31 | 452 |
| N49208 | 0.02 | 0.13 | 0.34 | 0.35 | 0.32 | 453 |
| XM_055699 | 0.05 | 0.02 | 0.23 | 0.36 | 0.39 | 454 |
| BC028234 | 0.02 | −0.45 | −0.24 | 0.26 | 0.37 | 455 |
| N89900 | 0.02 | −0.39 | −0.18 | 0.36 | 0.28 | 456 |
| NM_001278 | 0.00 | −0.63 | −0.42 | 0.22 | 0.21 | 457 |
| AI921613 | 0.01 | −0.06 | 0.16 | 0.25 | 0.26 | 458 |
| NM_003821 | 0.03 | −0.64 | −0.43 | 0.43 | 0.23 | 459 |
| XM_046035 | 0.00 | −0.37 | −0.16 | 0.20 | 0.27 | 460 |
| AI936300 | 0.04 | 0.08 | 0.29 | 0.30 | 0.39 | 461 |
| NM_003131 | 0.00 | −0.71 | −0.50 | 0.30 | 0.21 | 462 |
| R61546 | 0.01 | −0.52 | −0.31 | 0.30 | 0.25 | 463 |
| AA431750 | 0.02 | −0.24 | −0.03 | 0.32 | 0.29 | 464 |
| AI524099 | 0.00 | −0.03 | 0.18 | 0.15 | 0.20 | 465 |
| XM_042665 | 0.00 | 0.07 | 0.28 | 0.25 | 0.22 | 466 |
| AI820873 | 0.02 | −0.48 | −0.27 | 0.39 | 0.24 | 467 |
| NM_019011 | 0.02 | −0.60 | −0.39 | 0.27 | 0.35 | 468 |
| H51585 | 0.05 | −0.57 | −0.36 | 0.42 | 0.30 | 469 |
| AI393173 | 0.02 | −0.04 | 0.16 | 0.25 | 0.34 | 470 |
| AI560205 | 0.00 | −0.36 | −0.15 | 0.19 | 0.23 | 471 |
| AA429020 | 0.00 | −0.31 | −0.11 | 0.20 | 0.17 | 472 |
| NM_000681.2 | 0.01 | 0.14 | 0.34 | 0.30 | 0.27 | 473 |
| NM_014550 | 0.00 | −0.10 | 0.10 | 0.25 | 0.16 | 474 |
| AA453256 | 0.00 | −0.04 | 0.16 | 0.20 | 0.26 | 475 |
| NM_021138 | 0.00 | −0.23 | −0.03 | 0.28 | 0.14 | 476 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| R51304 | 0.05 | −0.02 | 0.19 | 0.32 | 0.38 | 477 |
| AI59011 | 0.00 | −0.31 | −0.10 | 0.14 | 0.20 | 478 |
| H09305 | 0.01 | −0.57 | −0.37 | 0.31 | 0.26 | 479 |
| R99076 | 0.00 | −0.40 | −0.19 | 0.19 | 0.22 | 480 |
| AI559096 | 0.01 | 0.28 | 0.48 | 0.29 | 0.29 | 481 |
| AI610213 | 0.02 | −0.12 | 0.08 | 0.34 | 0.27 | 482 |
| N66038 | 0.00 | −0.33 | −0.12 | 0.17 | 0.20 | 483 |
| NM_002649 | 0.00 | −0.33 | −0.13 | 0.17 | 0.29 | 484 |
| NM_006676 | 0.02 | −0.54 | −0.34 | 0.32 | 0.27 | 485 |
| NM_014959 | 0.00 | −0.38 | −0.18 | 0.24 | 0.25 | 486 |
| BC013992 | 0.01 | 0.01 | 0.21 | 0.16 | 0.32 | 487 |
| N32057 | 0.02 | −0.34 | −0.14 | 0.39 | 0.20 | 488 |
| AI801695 | 0.00 | −0.33 | −0.13 | 0.17 | 0.18 | 489 |
| AI568793 | 0.03 | 0.11 | 0.31 | 0.29 | 0.33 | 490 |
| AA479285 | 0.00 | 0.08 | 0.27 | 0.23 | 0.23 | 491 |
| H06501 | 0.02 | −0.10 | 0.10 | 0.32 | 0.28 | 492 |
| R00259 | 0.03 | −0.06 | 0.14 | 0.31 | 0.32 | 493 |
| AI362368 | 0.00 | −0.33 | −0.13 | 0.17 | 0.19 | 494 |
| AI635040 | 0.00 | −0.14 | 0.06 | 0.18 | 0.26 | 495 |
| AI354869 | 0.03 | −0.48 | −0.29 | 0.32 | 0.26 | 496 |
| N71407 | 0.02 | 0.06 | 0.25 | 0.26 | 0.32 | 497 |
| XM_038544 | 0.04 | −0.12 | 0.07 | 0.38 | 0.29 | 498 |
| NM_031910 | 0.04 | 0.18 | 0.38 | 0.27 | 0.38 | 499 |
| AI862063 | 0.00 | −0.28 | −0.08 | 0.20 | 0.24 | 500 |
| AA455638 | 0.03 | 0.07 | 0.27 | 0.28 | 0.32 | 501 |
| AI697430 | 0.00 | −0.36 | −0.17 | 0.18 | 0.21 | 502 |
| R42480 | 0.01 | −0.49 | −0.29 | 0.25 | 0.23 | 503 |
| AI674115 | 0.01 | 0.02 | 0.21 | 0.24 | 0.29 | 504 |
| AA968926 | 0.03 | −0.32 | −0.13 | 0.37 | 0.26 | 505 |
| AI524694 | 0.00 | −0.38 | −0.19 | 0.18 | 0.23 | 506 |
| AA609857 | 0.02 | −0.08 | 0.12 | 0.30 | 0.29 | 507 |
| AI913713 | 0.01 | −0.46 | −0.27 | 0.33 | 0.21 | 508 |
| W04695 | 0.00 | −0.28 | −0.09 | 0.16 | 0.24 | 509 |
| NM_033012 | 0.04 | −0.12 | 0.07 | 0.35 | 0.31 | 510 |
| T77048 | 0.02 | −0.01 | 0.18 | 0.26 | 0.31 | 511 |
| AI817381 | 0.01 | −0.25 | −0.06 | 0.23 | 0.24 | 512 |
| AI624918 | 0.03 | −0.02 | 0.17 | 0.28 | 0.32 | 513 |
| AI888072 | 0.01 | −0.26 | −0.07 | 0.23 | 0.26 | 514 |
| AA883759 | 0.00 | −0.38 | −0.20 | 0.21 | 0.22 | 515 |
| AA478611 | 0.00 | −0.34 | −0.15 | 0.25 | 0.17 | 516 |
| AI452862 | 0.03 | −0.28 | −0.09 | 0.34 | 0.26 | 517 |
| AI277955 | 0.00 | −0.46 | −0.27 | 0.24 | 0.22 | 518 |
| AI520967 | 0.00 | −0.34 | −0.15 | 0.17 | 0.20 | 519 |
| T91937 | 0.05 | 0.36 | 0.54 | 0.27 | 0.37 | 520 |
| AA993698 | 0.00 | 0.01 | 0.20 | 0.21 | 0.20 | 521 |
| AI620374 | 0.00 | −0.40 | −0.22 | 0.18 | 0.22 | 522 |
| AA707628 | 0.00 | −0.27 | −0.08 | 0.12 | 0.17 | 523 |
| AI572545 | 0.01 | −0.38 | −0.19 | 0.17 | 0.28 | 524 |
| AI801540 | 0.04 | −0.16 | 0.03 | 0.36 | 0.28 | 525 |
| AI354889 | 0.00 | −0.11 | 0.07 | 0.22 | 0.18 | 526 |
| NM_030751 | 0.03 | −0.09 | 0.09 | 0.33 | 0.25 | 527 |
| NM_000657 | 0.01 | −0.50 | −0.32 | 0.27 | 0.22 | 528 |
| AA045139 | 0.02 | −0.43 | −0.24 | 0.34 | 0.23 | 529 |
| AI912148 | 0.00 | −0.25 | −0.06 | 0.18 | 0.20 | 530 |
| AA513806 | 0.04 | −0.21 | −0.03 | 0.29 | 0.32 | 531 |
| H48440 | 0.00 | −0.35 | −0.17 | 0.16 | 0.23 | 532 |
| AA114117 | 0.00 | −0.38 | −0.20 | 0.17 | 0.18 | 533 |
| AI654471 | 0.00 | −0.20 | −0.02 | 0.19 | 0.20 | 534 |
| AA423792 | 0.00 | −0.16 | 0.02 | 0.14 | 0.25 | 535 |
| AI926484 | 0.00 | −0.08 | 0.10 | 0.25 | 0.14 | 536 |
| T89979 | 0.00 | −0.30 | −0.12 | 0.16 | 0.19 | 537 |
| AI889310 | 0.01 | −0.25 | −0.07 | 0.26 | 0.21 | 538 |
| R11261 | 0.04 | −0.27 | −0.09 | 0.43 | 0.18 | 539 |
| AI932551 | 0.00 | −0.32 | −0.14 | 0.16 | 0.23 | 540 |
| NM_017626.1 | 0.01 | −0.56 | −0.38 | 0.22 | 0.26 | 541 |
| AI381513 | 0.04 | −0.29 | −0.11 | 0.32 | 0.29 | 542 |
| AA682407 | 0.02 | −0.24 | −0.07 | 0.25 | 0.29 | 543 |
| AA954316 | 0.04 | −0.75 | −0.57 | 0.35 | 0.27 | 544 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
|---|---|---|---|---|---|---|
| | | Group of patients with non-infectious MOF | Group of patients with infectious MOF | Group of patients with non-infectious MOF | Group of patients with infectious MOF | |
| AI791500 | 0.02 | 0.16 | 0.34 | 0.18 | 0.31 | 545 |
| T91881 | 0.00 | −0.26 | −0.08 | 0.18 | 0.23 | 546 |
| AI149857 | 0.02 | −0.06 | 0.12 | 0.18 | 0.30 | 547 |
| AI370842 | 0.04 | 0.11 | 0.29 | 0.31 | 0.30 | 548 |
| AA401205 | 0.00 | −0.13 | 0.05 | 0.18 | 0.19 | 549 |
| AA453267 | 0.02 | −0.03 | 0.15 | 0.26 | 0.28 | 550 |
| R88475 | 0.00 | −0.35 | −0.17 | 0.18 | 0.20 | 551 |
| AI864919 | 0.01 | −0.38 | −0.20 | 0.19 | 0.25 | 552 |
| NM_002169 | 0.04 | −0.24 | −0.07 | 0.33 | 0.27 | 553 |
| R46801 | 0.05 | 0.27 | 0.44 | 0.35 | 0.27 | 554 |
| AI277856 | 0.02 | −0.12 | 0.06 | 0.22 | 0.27 | 555 |
| H22921 | 0.00 | −0.33 | −0.15 | 0.19 | 0.22 | 556 |
| AI763386 | 0.03 | −0.37 | −0.20 | 0.30 | 0.27 | 557 |
| N78812 | 0.01 | −0.23 | −0.06 | 0.25 | 0.20 | 558 |
| H83981 | 0.04 | 0.04 | 0.22 | 0.28 | 0.30 | 559 |
| AA029887 | 0.00 | −0.40 | −0.22 | 0.19 | 0.21 | 560 |
| AI192112 | 0.00 | −0.11 | 0.06 | 0.15 | 0.24 | 561 |
| W88960 | 0.01 | 0.10 | 0.28 | 0.21 | 0.24 | 562 |
| W80744 | 0.00 | −0.25 | −0.08 | 0.15 | 0.21 | 563 |
| AI521577 | 0.01 | −0.31 | −0.13 | 0.18 | 0.23 | 564 |
| AA418572 | 0.01 | −0.13 | 0.05 | 0.17 | 0.25 | 565 |
| N73510 | 0.00 | −0.38 | −0.21 | 0.17 | 0.22 | 566 |
| AI631299 | 0.03 | −0.16 | 0.01 | 0.24 | 0.29 | 567 |
| XM_012717 | 0.00 | −0.44 | −0.27 | 0.18 | 0.17 | 568 |
| NM_000590 | 0.03 | 0.32 | 0.50 | 0.23 | 0.29 | 569 |
| AI381910 | 0.01 | −0.04 | 0.13 | 0.21 | 0.23 | 570 |
| R87714 | 0.04 | −0.18 | −0.01 | 0.33 | 0.23 | 571 |
| AA609628 | 0.00 | −0.36 | −0.19 | 0.17 | 0.19 | 572 |
| AA634317 | 0.03 | 0.19 | 0.36 | 0.27 | 0.28 | 573 |
| AI214830 | 0.04 | −0.27 | −0.10 | 0.23 | 0.32 | 574 |
| AI203201 | 0.04 | −0.26 | −0.09 | 0.26 | 0.29 | 575 |
| AI924806 | 0.00 | −0.29 | −0.12 | 0.20 | 0.18 | 576 |
| AA701319 | 0.02 | −0.07 | 0.10 | 0.22 | 0.28 | 577 |
| N63628 | 0.03 | −0.26 | −0.09 | 0.26 | 0.27 | 578 |
| R02742 | 0.04 | −0.17 | −0.01 | 0.32 | 0.25 | 579 |
| H07860 | 0.02 | −0.03 | 0.13 | 0.26 | 0.24 | 580 |
| H77534 | 0.02 | −0.35 | −0.18 | 0.32 | 0.20 | 581 |
| AI208537 | 0.02 | −0.21 | −0.04 | 0.34 | 0.17 | 582 |
| AI184715 | 0.01 | −0.03 | 0.13 | 0.23 | 0.20 | 583 |
| R05816 | 0.00 | −0.27 | −0.10 | 0.19 | 0.20 | 584 |
| AA961252 | 0.04 | −0.14 | 0.02 | 0.26 | 0.31 | 585 |
| AI801425 | 0.00 | −0.21 | −0.04 | 0.22 | 0.17 | 586 |
| AA477776 | 0.01 | −0.01 | 0.16 | 0.21 | 0.20 | 587 |
| R06585 | 0.01 | −0.40 | −0.23 | 0.18 | 0.21 | 588 |
| AA405788 | 0.01 | −0.36 | −0.19 | 0.15 | 0.25 | 589 |
| R06107 | 0.01 | −0.23 | −0.07 | 0.24 | 0.19 | 590 |
| AA923316 | 0.00 | −0.20 | −0.04 | 0.15 | 0.19 | 591 |
| AI421397 | 0.02 | −0.02 | 0.14 | 0.19 | 0.26 | 592 |
| NM_006881 | 0.01 | −0.40 | −0.24 | 0.20 | 0.23 | 593 |
| R43415 | 0.00 | −0.24 | −0.08 | 0.14 | 0.19 | 594 |
| H11495 | 0.01 | −0.29 | −0.12 | 0.26 | 0.13 | 595 |
| AI208772 | 0.04 | −0.23 | −0.07 | 0.29 | 0.27 | 596 |
| AA479784 | 0.03 | −0.06 | 0.10 | 0.29 | 0.24 | 597 |
| AA485092 | 0.00 | −0.36 | −0.20 | 0.16 | 0.20 | 598 |
| AA664688 | 0.00 | −0.39 | −0.23 | 0.18 | 0.20 | 599 |
| H48230 | 0.01 | −0.29 | −0.13 | 0.19 | 0.21 | 600 |
| AI248075 | 0.02 | −0.12 | 0.04 | 0.25 | 0.22 | 601 |
| AA418695 | 0.04 | −0.01 | 0.15 | 0.21 | 0.31 | 602 |
| AI673731 | 0.01 | −0.41 | −0.25 | 0.16 | 0.22 | 603 |
| XM_008948 | 0.03 | 0.10 | 0.26 | 0.26 | 0.26 | 604 |
| AI301257 | 0.00 | −0.31 | −0.15 | 0.19 | 0.19 | 605 |
| NM_003823 | 0.04 | −0.72 | −0.56 | 0.31 | 0.24 | 606 |
| AI744264 | 0.01 | −0.14 | 0.02 | 0.16 | 0.22 | 607 |
| AI809873 | 0.03 | −0.45 | −0.29 | 0.24 | 0.26 | 608 |
| AI354243 | 0.01 | −0.34 | −0.18 | 0.17 | 0.21 | 609 |
| NM_001553.1 | 0.04 | −0.15 | 0.01 | 0.27 | 0.27 | 610 |
| W86575 | 0.02 | −0.34 | −0.18 | 0.23 | 0.24 | 611 |
| AA442720 | 0.03 | −0.15 | 0.01 | 0.27 | 0.24 | 612 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AA993597 | 0.03 | 0.17 | 0.33 | 0.26 | 0.24 | 613 |
| AI433952 | 0.01 | −0.30 | −0.14 | 0.16 | 0.23 | 614 |
| R56800 | 0.01 | −0.09 | 0.06 | 0.17 | 0.21 | 615 |
| AA417031 | 0.01 | −0.21 | −0.06 | 0.19 | 0.23 | 616 |
| R53961 | 0.04 | −0.45 | −0.29 | 0.28 | 0.25 | 617 |
| T86887 | 0.00 | −0.23 | −0.08 | 0.13 | 0.20 | 618 |
| AA705808 | 0.01 | −0.20 | −0.04 | 0.25 | 0.18 | 619 |
| AA426451 | 0.00 | −0.28 | −0.13 | 0.16 | 0.19 | 620 |
| H06263 | 0.00 | −0.28 | −0.12 | 0.14 | 0.17 | 621 |
| AA659421 | 0.00 | −0.32 | −0.17 | 0.14 | 0.16 | 622 |
| AI801595 | 0.00 | −0.28 | −0.13 | 0.16 | 0.19 | 623 |
| AI672318 | 0.04 | −0.20 | −0.05 | 0.31 | 0.24 | 624 |
| AI762019 | 0.01 | −0.25 | −0.09 | 0.19 | 0.21 | 625 |
| N92873 | 0.02 | −0.11 | 0.05 | 0.28 | 0.19 | 626 |
| NM_017442 | 0.04 | 0.08 | 0.23 | 0.28 | 0.25 | 627 |
| H46164 | 0.03 | 0.03 | 0.18 | 0.21 | 0.27 | 628 |
| T83946 | 0.01 | −0.29 | −0.14 | 0.20 | 0.21 | 629 |
| AA868726 | 0.04 | −0.42 | −0.27 | 0.26 | 0.25 | 630 |
| H88129 | 0.02 | −0.37 | −0.22 | 0.21 | 0.23 | 631 |
| R88267 | 0.04 | −0.12 | 0.03 | 0.30 | 0.23 | 632 |
| AI798545 | 0.01 | −0.32 | −0.17 | 0.17 | 0.19 | 633 |
| N57775 | 0.02 | −0.14 | 0.01 | 0.22 | 0.22 | 634 |
| AA425134 | 0.00 | −0.21 | −0.07 | 0.16 | 0.19 | 635 |
| AI744807 | 0.01 | −0.59 | −0.44 | 0.20 | 0.22 | 636 |
| AI702056 | 0.05 | −0.27 | −0.12 | 0.22 | 0.29 | 637 |
| NM_000575 | 0.04 | −0.27 | −0.12 | 0.23 | 0.25 | 638 |
| T98779 | 0.01 | −0.38 | −0.23 | 0.18 | 0.23 | 639 |
| NM_000587 | 0.01 | −0.43 | −0.28 | 0.18 | 0.19 | 640 |
| R92455 | 0.01 | −0.36 | −0.21 | 0.17 | 0.21 | 641 |
| AI758473 | 0.01 | −0.36 | −0.21 | 0.18 | 0.22 | 642 |
| AA398364 | 0.00 | −0.31 | −0.17 | 0.13 | 0.21 | 643 |
| AI811774 | 0.05 | 0.20 | 0.35 | 0.23 | 0.27 | 644 |
| AI299411 | 0.00 | −0.24 | −0.10 | 0.17 | 0.18 | 645 |
| AA225138 | 0.00 | −0.26 | −0.11 | 0.12 | 0.17 | 646 |
| AA418689 | 0.05 | 0.09 | 0.24 | 0.21 | 0.28 | 647 |
| T77995 | 0.01 | −0.18 | −0.04 | 0.21 | 0.20 | 648 |
| AA808788 | 0.04 | −0.33 | −0.18 | 0.18 | 0.25 | 649 |
| AI677645 | 0.01 | −0.25 | −0.11 | 0.15 | 0.19 | 650 |
| AA629306 | 0.04 | −0.07 | 0.07 | 0.26 | 0.24 | 651 |
| AA749151 | 0.00 | −0.19 | −0.05 | 0.13 | 0.17 | 652 |
| AI679294 | 0.01 | −0.41 | −0.27 | 0.19 | 0.19 | 653 |
| R45611 | 0.02 | −0.24 | −0.10 | 0.16 | 0.24 | 654 |
| NM_000588 | 0.05 | −0.18 | −0.04 | 0.29 | 0.22 | 655 |
| H99483 | 0.01 | −0.29 | −0.15 | 0.16 | 0.22 | 656 |
| AI679923 | 0.01 | −0.46 | −0.32 | 0.17 | 0.20 | 657 |
| AI077580 | 0.05 | −0.04 | 0.10 | 0.27 | 0.23 | 658 |
| D49410 | 0.01 | −0.31 | −0.17 | 0.19 | 0.19 | 659 |
| AI692267 | 0.04 | −0.42 | −0.28 | 0.22 | 0.24 | 660 |
| AI804001 | 0.02 | 0.00 | 0.14 | 0.19 | 0.23 | 661 |
| T87188 | 0.01 | −0.32 | −0.18 | 0.19 | 0.19 | 662 |
| AI368218 | 0.02 | −0.24 | −0.10 | 0.13 | 0.23 | 663 |
| AI208749 | 0.02 | −0.02 | 0.11 | 0.22 | 0.19 | 664 |
| H61046 | 0.02 | −0.21 | −0.07 | 0.18 | 0.22 | 665 |
| NM_001330.1 | 0.01 | −0.05 | 0.08 | 0.19 | 0.20 | 666 |
| XM_001322 | 0.01 | −0.33 | −0.19 | 0.18 | 0.17 | 667 |
| NM_004195 | 0.04 | 0.23 | 0.37 | 0.16 | 0.27 | 668 |
| AI285713 | 0.01 | −0.32 | −0.18 | 0.15 | 0.21 | 669 |
| AA527369 | 0.00 | −0.13 | 0.00 | 0.15 | 0.16 | 670 |
| AI350069 | 0.01 | −0.24 | −0.11 | 0.15 | 0.21 | 671 |
| AI493975 | 0.01 | −0.24 | −0.10 | 0.18 | 0.16 | 672 |
| AI355007 | 0.03 | −0.23 | −0.10 | 0.22 | 0.21 | 673 |
| AA225239 | 0.04 | −0.40 | −0.26 | 0.21 | 0.25 | 674 |
| AA001392 | 0.03 | −0.39 | −0.26 | 0.24 | 0.19 | 675 |
| AI933797 | 0.02 | −0.28 | −0.15 | 0.22 | 0.18 | 676 |
| R43065 | 0.01 | −0.21 | −0.08 | 0.16 | 0.18 | 677 |
| AA478621 | 0.03 | −0.21 | −0.08 | 0.21 | 0.20 | 678 |
| AA012850 | 0.03 | −0.32 | −0.19 | 0.17 | 0.22 | 679 |
| AI925035 | 0.03 | −0.15 | −0.02 | 0.17 | 0.23 | 680 |

TABLE 3-continued

Significantly increased gene activities in samples of patients with infectious MOF, if compared with the gene activities of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AA995218 | 0.03 | −0.22 | −0.09 | 0.19 | 0.21 | 681 |
| AA897716 | 0.04 | −0.18 | −0.06 | 0.23 | 0.21 | 682 |
| AA983987 | 0.02 | −0.28 | −0.15 | 0.18 | 0.18 | 683 |
| AI762202 | 0.03 | −0.18 | −0.05 | 0.22 | 0.20 | 684 |
| T95909 | 0.02 | −0.34 | −0.22 | 0.18 | 0.19 | 685 |
| N22551 | 0.03 | −0.36 | −0.24 | 0.17 | 0.22 | 686 |
| AI769053 | 0.03 | −0.28 | −0.15 | 0.15 | 0.22 | 687 |
| AF039955 | 0.01 | −0.37 | −0.24 | 0.20 | 0.16 | 688 |
| AI935874 | 0.02 | −0.26 | −0.14 | 0.16 | 0.20 | 689 |
| AI570779 | 0.01 | −0.31 | −0.19 | 0.15 | 0.18 | 690 |
| AI240539 | 0.01 | −0.22 | −0.09 | 0.17 | 0.18 | 691 |
| H54423 | 0.03 | −0.32 | −0.20 | 0.16 | 0.22 | 692 |
| AA460136 | 0.02 | −0.09 | 0.03 | 0.24 | 0.14 | 693 |
| NM_033357 | 0.05 | −0.24 | −0.12 | 0.19 | 0.23 | 694 |
| AI923479 | 0.04 | −0.30 | −0.18 | 0.20 | 0.22 | 695 |
| H18944 | 0.04 | −0.42 | −0.30 | 0.21 | 0.19 | 696 |
| NM_006509 | 0.03 | 0.01 | 0.13 | 0.12 | 0.23 | 697 |
| AI865298 | 0.02 | −0.31 | −0.19 | 0.13 | 0.20 | 698 |
| AI123502 | 0.04 | −0.36 | −0.24 | 0.17 | 0.22 | 699 |
| AI885918 | 0.02 | −0.24 | −0.12 | 0.14 | 0.19 | 700 |
| AA225023 | 0.02 | −0.33 | −0.21 | 0.12 | 0.20 | 701 |
| AA421020 | 0.04 | −0.25 | −0.13 | 0.19 | 0.21 | 702 |
| AJ297560 | 0.05 | −0.29 | −0.17 | 0.21 | 0.20 | 703 |
| N95217 | 0.02 | −0.30 | −0.19 | 0.12 | 0.19 | 704 |
| AA526032 | 0.04 | −0.25 | −0.13 | 0.20 | 0.19 | 705 |
| AA496309 | 0.02 | −0.32 | −0.20 | 0.15 | 0.19 | 706 |
| AI732958 | 0.03 | −0.22 | −0.11 | 0.18 | 0.18 | 707 |
| AA410828 | 0.02 | −0.29 | −0.18 | 0.20 | 0.16 | 708 |
| AA453993 | 0.02 | −0.30 | −0.19 | 0.18 | 0.16 | 709 |
| R92993 | 0.02 | −0.26 | −0.15 | 0.12 | 0.19 | 710 |
| NM_003921 | 0.04 | −0.23 | −0.13 | 0.20 | 0.18 | 711 |
| AI379967 | 0.02 | −0.34 | −0.23 | 0.15 | 0.17 | 712 |
| AI926656 | 0.04 | −0.26 | −0.15 | 0.18 | 0.19 | 713 |
| AA935872 | 0.03 | −0.31 | −0.20 | 0.16 | 0.18 | 714 |
| H08791 | 0.03 | −0.27 | −0.17 | 0.16 | 0.18 | 715 |
| AI932884 | 0.03 | −0.31 | −0.21 | 0.16 | 0.18 | 716 |
| AI926745 | 0.03 | −0.33 | −0.22 | 0.18 | 0.16 | 717 |
| R99595 | 0.05 | −0.29 | −0.19 | 0.16 | 0.20 | 718 |
| AI824579 | 0.03 | −0.31 | −0.21 | 0.13 | 0.18 | 719 |
| AA427886 | 0.03 | −0.27 | −0.17 | 0.14 | 0.16 | 720 |
| H42488 | 0.04 | −0.33 | −0.24 | 0.16 | 0.15 | 721 |

TABLE 4

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| NM_019111 | 0.00 | 1.41 | 0.21 | 0.73 | 0.56 | 722 |
| N29761 | 0.00 | −0.25 | −1.35 | 0.61 | 0.92 | 723 |
| NM_002124 | 0.00 | 1.60 | 0.54 | 0.62 | 0.52 | 724 |
| R43910 | 0.00 | 2.51 | 1.49 | 1.25 | 0.88 | 725 |
| NM_000570 | 0.00 | 3.66 | 2.67 | 0.70 | 1.31 | 726 |
| NM_002923 | 0.00 | 2.03 | 1.07 | 0.83 | 0.89 | 727 |
| X00457 | 0.00 | 1.46 | 0.50 | 0.84 | 0.60 | 728 |
| NM_022555 | 0.00 | 1.86 | 0.91 | 0.58 | 0.54 | 729 |
| NM_002125 | 0.00 | 1.38 | 0.46 | 0.55 | 0.45 | 730 |

TABLE 4-continued

Significantly reduced gene activities in samples of patients with infectious MOF, if compared with the gene activites of patients with non-infectious MOF.

| | | Mean normalised and transformed expression value | | Standard deviation | | |
|---|---|---|---|---|---|---|
| GenBank Accession No. | p-value | Group of patients with non-infectious MOF | Group of patients with infectious MOF | Group of patients with non-infectious MOF | Group of patients with infectious MOF | SEQUENCE-ID |
| AA620760 | 0.00 | 0.30 | −0.62 | 0.47 | 0.60 | 731 |
| NM_000569 | 0.01 | 3.13 | 2.26 | 0.86 | 1.21 | 732 |
| NM_021983 | 0.00 | 1.38 | 0.52 | 0.48 | 0.41 | 733 |
| R43203 | 0.00 | 2.03 | 1.18 | 1.16 | 0.74 | 734 |
| NM_033554 | 0.00 | 1.42 | 0.60 | 0.60 | 0.52 | 735 |
| AA626239 | 0.00 | 0.15 | −0.65 | 0.74 | 0.73 | 736 |
| NM_007328 | 0.00 | −0.31 | −1.10 | 0.49 | 0.64 | 737 |
| M90746 | 0.02 | 3.67 | 2.89 | 0.74 | 1.37 | 738 |
| T91086 | 0.00 | −0.81 | −1.59 | 0.63 | 0.67 | 739 |
| AA151104 | 0.00 | 0.11 | −0.64 | 0.46 | 0.46 | 740 |
| H45298 | 0.01 | 1.84 | 1.09 | 0.90 | 0.97 | 741 |
| NM_031311 | 0.00 | 0.78 | 0.03 | 0.52 | 0.39 | 742 |
| AI590144 | 0.00 | 1.70 | 0.96 | 0.97 | 0.70 | 743 |
| NM_001824.2 | 0.00 | 1.63 | 0.88 | 0.58 | 0.67 | 744 |
| NM_018643 | 0.00 | 1.70 | 0.96 | 0.54 | 0.66 | 745 |
| AA400790 | 0.00 | 0.93 | 0.20 | 0.59 | 0.52 | 746 |
| NM_001251 | 0.00 | 1.18 | 0.47 | 0.42 | 0.48 | 747 |
| NM_000887.2 | 0.00 | 0.24 | −0.48 | 0.92 | 0.61 | 748 |
| AI696291 | 0.00 | 0.74 | 0.04 | 0.64 | 0.39 | 749 |
| NM_031477 | 0.02 | 1.89 | 1.19 | 1.02 | 1.06 | 750 |
| AA910846 | 0.00 | 1.29 | 0.60 | 0.87 | 0.45 | 751 |
| NM_005538 | 0.00 | 1.59 | 0.91 | 0.90 | 0.72 | 752 |
| AA398331 | 0.00 | 0.13 | −0.53 | 0.51 | 0.46 | 753 |
| NM_025139 | 0.04 | −1.79 | −2.41 | 0.75 | 1.17 | 754 |
| AA398611 | 0.00 | 1.16 | 0.54 | 0.77 | 0.43 | 755 |
| NM_006682 | 0.00 | −0.05 | −0.67 | 0.46 | 0.39 | 756 |
| X52473 | 0.00 | 1.71 | 1.09 | 0.59 | 0.74 | 757 |
| AI859777 | 0.01 | −1.02 | −1.63 | 0.87 | 0.77 | 758 |
| H18649 | 0.00 | −0.41 | −1.01 | 0.30 | 0.58 | 759 |
| AI700444 | 0.00 | 1.57 | 0.97 | 0.70 | 0.63 | 760 |
| XM_001472 | 0.00 | −0.36 | −0.95 | 0.61 | 0.59 | 761 |
| XM_049959 | 0.01 | 2.10 | 1.53 | 0.73 | 0.78 | 762 |
| AA863064 | 0.03 | 0.96 | 0.39 | 1.20 | 0.63 | 763 |
| H88328 | 0.01 | −1.27 | −1.84 | 0.73 | 0.69 | 764 |
| R40861 | 0.00 | 0.82 | 0.25 | 0.82 | 0.51 | 765 |
| AI733498 | 0.00 | −0.37 | −0.93 | 0.36 | 0.58 | 766 |
| NM_002621 | 0.01 | 1.16 | 0.61 | 0.63 | 0.70 | 767 |
| AI732971 | 0.00 | 0.46 | −0.09 | 0.55 | 0.35 | 768 |
| AA813145 | 0.00 | 0.48 | −0.07 | 0.40 | 0.41 | 769 |
| NM_004221.2 | 0.02 | 2.05 | 1.51 | 0.75 | 0.79 | 770 |
| AA740907 | 0.00 | 0.05 | −0.49 | 0.44 | 0.32 | 771 |
| NM_032022 | 0.00 | 0.90 | 0.36 | 0.42 | 0.50 | 772 |
| XM_003789 | 0.00 | −0.25 | −0.78 | 0.37 | 0.47 | 773 |
| AI357099 | 0.02 | −1.06 | −1.59 | 0.85 | 0.78 | 774 |
| NM_003937 | 0.00 | −0.43 | −0.95 | 0.44 | 0.44 | 775 |
| NM_002122 | 0.00 | 0.84 | 0.33 | 0.71 | 0.51 | 776 |
| AI625626 | 0.01 | 0.90 | 0.40 | 0.87 | 0.52 | 777 |
| H23819 | 0.00 | 0.97 | 0.46 | 0.62 | 0.47 | 778 |
| AI797009 | 0.01 | 0.64 | 0.14 | 0.85 | 0.57 | 779 |
| XM_031354 | 0.01 | 0.99 | 0.49 | 0.63 | 0.72 | 780 |
| XM_051958 | 0.01 | 1.20 | 0.70 | 0.53 | 0.72 | 781 |
| AI499173 | 0.01 | 0.11 | −0.38 | 0.75 | 0.50 | 782 |
| NM_000591 | 0.00 | 0.92 | 0.43 | 0.50 | 0.55 | 783 |
| NM_057158 | 0.00 | −0.03 | −0.52 | 0.49 | 0.34 | 784 |
| R71775 | 0.00 | 0.42 | −0.07 | 0.61 | 0.55 | 785 |
| AI924028 | 0.00 | −0.35 | −0.84 | 0.36 | 0.58 | 786 |
| R39504 | 0.00 | −0.50 | −0.98 | 0.34 | 0.40 | 787 |
| N66205 | 0.01 | 1.49 | 1.02 | 0.72 | 0.62 | 788 |
| AI738831 | 0.00 | 0.09 | −0.38 | 0.29 | 0.56 | 789 |
| H18435 | 0.00 | 0.34 | −0.14 | 0.43 | 0.32 | 790 |
| R39782 | 0.00 | −0.35 | −0.82 | 0.44 | 0.35 | 791 |
| R38717 | 0.00 | −0.16 | −0.63 | 0.43 | 0.48 | 792 |
| H96798 | 0.00 | 0.19 | −0.27 | 0.47 | 0.53 | 793 |
| N72174 | 0.02 | 0.92 | 0.46 | 0.53 | 0.73 | 794 |
| AI739381 | 0.00 | −0.11 | −0.57 | 0.24 | 0.50 | 795 |
| AI654546 | 0.00 | 0.05 | −0.41 | 0.31 | 0.46 | 796 |
| AI097494 | 0.00 | −0.72 | −1.19 | 0.41 | 0.57 | 797 |
| NM_000612.2 | 0.00 | 0.93 | 0.47 | 0.50 | 0.36 | 798 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AI651536 | 0.00 | 0.62 | 0.16 | 0.50 | 0.29 | 799 |
| AI804425 | 0.00 | 0.90 | 0.44 | 0.73 | 0.38 | 800 |
| n67686 | 0.00 | 0.43 | −0.03 | 0.62 | 0.38 | 801 |
| NM_000062 | 0.01 | −0.18 | −0.63 | 0.75 | 0.45 | 802 |
| R54442 | 0.00 | 0.69 | 0.24 | 0.53 | 0.39 | 803 |
| AI475085 | 0.00 | 0.25 | −0.20 | 0.67 | 0.29 | 804 |
| AI700612 | 0.01 | −0.85 | −1.30 | 0.60 | 0.61 | 805 |
| AA447615 | 0.00 | 0.18 | −0.27 | 0.60 | 0.30 | 806 |
| AI223092 | 0.00 | −0.38 | −0.82 | 0.30 | 0.56 | 807 |
| AI262894 | 0.00 | 0.47 | 0.03 | 0.61 | 0.39 | 808 |
| R52949 | 0.01 | −1.08 | −1.52 | 0.44 | 0.72 | 809 |
| AA629034 | 0.00 | −0.13 | −0.57 | 0.37 | 0.33 | 810 |
| R12559 | 0.00 | 0.72 | 0.29 | 0.45 | 0.37 | 811 |
| AA910310 | 0.00 | 0.03 | −0.40 | 0.35 | 0.27 | 812 |
| NM_006850 | 0.01 | 0.19 | −0.24 | 0.59 | 0.51 | 813 |
| AI689080 | 0.05 | 1.34 | 0.91 | 0.74 | 0.78 | 814 |
| R23755 | 0.00 | 0.16 | −0.26 | 0.40 | 0.37 | 815 |
| N95041 | 0.00 | 0.17 | −0.25 | 0.30 | 0.40 | 816 |
| AA443712 | 0.01 | 0.76 | 0.34 | 0.72 | 0.41 | 817 |
| NM_033302 | 0.03 | 1.53 | 1.11 | 0.54 | 0.72 | 818 |
| AI700810 | 0.00 | 0.59 | 0.18 | 0.72 | 0.25 | 819 |
| XM_004011 | 0.00 | 0.52 | 0.11 | 0.44 | 0.35 | 820 |
| H11433 | 0.00 | 0.38 | −0.03 | 0.55 | 0.35 | 821 |
| NM_006890 | 0.03 | 1.14 | 0.73 | 0.77 | 0.52 | 822 |
| NM_138556 | 0.00 | 0.16 | −0.25 | 0.23 | 0.36 | 823 |
| XM_003937 | 0.00 | 0.13 | −0.28 | 0.34 | 0.33 | 824 |
| NM_000908.1 | 0.00 | −0.05 | −0.46 | 0.22 | 0.30 | 825 |
| NM_017567 | 0.01 | −0.52 | −0.92 | 0.57 | 0.47 | 826 |
| R89802 | 0.00 | −0.21 | −0.61 | 0.27 | 0.33 | 827 |
| NM_000715 | 0.01 | 0.77 | 0.37 | 0.56 | 0.46 | 828 |
| AI924733 | 0.00 | −0.60 | −1.00 | 0.37 | 0.50 | 829 |
| AI859370 | 0.00 | 0.17 | −0.23 | 0.16 | 0.24 | 830 |
| AI023558 | 0.00 | −0.41 | −0.80 | 0.23 | 0.37 | 831 |
| AA021303 | 0.00 | 0.19 | −0.20 | 0.58 | 0.25 | 832 |
| R69609 | 0.01 | 1.03 | 0.64 | 0.54 | 0.51 | 833 |
| XM_057445 | 0.00 | 0.27 | −0.12 | 0.35 | 0.39 | 834 |
| AA046302 | 0.00 | −0.10 | −0.49 | 0.36 | 0.33 | 835 |
| AI383451 | 0.01 | 0.26 | −0.13 | 0.53 | 0.40 | 836 |
| AA464191 | 0.00 | −0.46 | −0.84 | 0.32 | 0.41 | 837 |
| AA425808 | 0.00 | −0.22 | −0.61 | 0.25 | 0.51 | 838 |
| XM_038024 | 0.00 | 0.18 | −0.21 | 0.28 | 0.47 | 839 |
| AI016127 | 0.01 | 1.07 | 0.69 | 0.56 | 0.42 | 840 |
| AA400144 | 0.03 | −0.41 | −0.79 | 0.60 | 0.62 | 841 |
| R43074 | 0.00 | −0.99 | −1.36 | 0.28 | 0.51 | 842 |
| AI628936 | 0.01 | −0.65 | −1.03 | 0.41 | 0.51 | 843 |
| AA461499 | 0.00 | −0.16 | −0.54 | 0.39 | 0.38 | 844 |
| AI668673 | 0.00 | 0.34 | −0.03 | 0.35 | 0.50 | 845 |
| AI539443 | 0.00 | 0.24 | −0.13 | 0.39 | 0.43 | 846 |
| AA404231 | 0.04 | −0.14 | −0.52 | 0.52 | 0.69 | 847 |
| AI692869 | 0.01 | 0.72 | 0.34 | 0.30 | 0.53 | 848 |
| AI822099 | 0.00 | 0.00 | −0.37 | 0.51 | 0.34 | 849 |
| R20616 | 0.00 | 0.12 | −0.25 | 0.30 | 0.32 | 850 |
| AA453406 | 0.01 | −0.66 | −1.03 | 0.42 | 0.49 | 851 |
| AA282404 | 0.02 | 0.07 | −0.29 | 0.46 | 0.58 | 852 |
| AI023336 | 0.00 | 0.24 | −0.13 | 0.28 | 0.27 | 853 |
| NM_001964 | 0.02 | −0.63 | −0.99 | 0.56 | 0.53 | 854 |
| N35603 | 0.04 | −0.51 | −0.87 | 0.51 | 0.67 | 855 |
| AI632210 | 0.00 | 0.35 | −0.01 | 0.60 | 0.26 | 856 |
| AA156454 | 0.00 | 0.37 | 0.01 | 0.34 | 0.35 | 857 |
| AA620836 | 0.02 | 0.24 | −0.12 | 0.51 | 0.55 | 858 |
| NM_020530 | 0.00 | 0.37 | 0.01 | 0.44 | 0.30 | 859 |
| AA928277 | 0.00 | −0.10 | −0.46 | 0.34 | 0.36 | 860 |
| NM_001559 | 0.04 | 0.37 | 0.01 | 0.73 | 0.50 | 861 |
| AA401691 | 0.00 | −0.08 | −0.44 | 0.39 | 0.38 | 862 |
| NM_015991 | 0.00 | 0.01 | −0.34 | 0.46 | 0.33 | 863 |
| N80764 | 0.00 | −0.08 | −0.43 | 0.33 | 0.43 | 864 |
| L34657 | 0.00 | 0.12 | −0.23 | 0.31 | 0.34 | 865 |
| H98244 | 0.00 | 0.24 | −0.11 | 0.39 | 0.35 | 866 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AA894523 | 0.00 | −0.24 | −0.59 | 0.23 | 0.29 | 867 |
| NM_013261.1 | 0.00 | 0.08 | −0.26 | 0.32 | 0.37 | 868 |
| H02254 | 0.01 | −0.39 | −0.73 | 0.40 | 0.45 | 869 |
| NM_003781.2 | 0.01 | −0.64 | −0.98 | 0.50 | 0.36 | 870 |
| NM_001243 | 0.05 | 0.78 | 0.44 | 0.51 | 0.66 | 871 |
| AA442897 | 0.01 | −0.44 | −0.78 | 0.32 | 0.46 | 872 |
| T85314 | 0.01 | −0.29 | −0.63 | 0.46 | 0.43 | 873 |
| AI658519 | 0.05 | 0.50 | 0.16 | 0.70 | 0.50 | 874 |
| AI207975 | 0.00 | −0.28 | −0.62 | 0.37 | 0.30 | 875 |
| AI536602 | 0.00 | 0.28 | −0.06 | 0.47 | 0.33 | 876 |
| NM_001541.1 | 0.00 | 0.50 | 0.16 | 0.38 | 0.27 | 877 |
| AA992540 | 0.00 | 0.14 | −0.19 | 0.31 | 0.32 | 878 |
| Z22971 | 0.01 | 0.62 | 0.29 | 0.51 | 0.39 | 879 |
| AI560847 | 0.00 | 0.36 | 0.03 | 0.23 | 0.28 | 880 |
| XM_008346 | 0.04 | 0.40 | 0.07 | 0.59 | 0.54 | 881 |
| AA015795 | 0.02 | −0.36 | −0.69 | 0.57 | 0.42 | 882 |
| R00742 | 0.00 | 0.37 | 0.04 | 0.34 | 0.33 | 883 |
| H16774 | 0.00 | 0.02 | −0.31 | 0.33 | 0.24 | 884 |
| R51373 | 0.00 | 0.15 | −0.18 | 0.31 | 0.24 | 885 |
| AI479659 | 0.00 | 0.18 | −0.14 | 0.34 | 0.29 | 886 |
| W58195 | 0.00 | −0.06 | −0.39 | 0.27 | 0.39 | 887 |
| NM_004437.1 | 0.05 | 1.06 | 0.73 | 0.47 | 0.65 | 888 |
| AA479357 | 0.00 | 0.18 | −0.15 | 0.30 | 0.21 | 889 |
| AI423518 | 0.00 | −0.25 | −0.57 | 0.29 | 0.40 | 890 |
| NM_002750 | 0.01 | −0.52 | −0.85 | 0.36 | 0.44 | 891 |
| R26444 | 0.00 | 0.00 | −0.32 | 0.27 | 0.36 | 892 |
| AA136071 | 0.00 | 0.04 | −0.29 | 0.25 | 0.34 | 893 |
| AI554459 | 0.00 | −0.02 | −0.34 | 0.39 | 0.35 | 894 |
| N51537 | 0.02 | 0.89 | 0.57 | 0.45 | 0.49 | 895 |
| NM_006068 | 0.00 | 0.62 | 0.30 | 0.35 | 0.39 | 896 |
| NM_016184 | 0.03 | 0.61 | 0.29 | 0.49 | 0.52 | 897 |
| NM_000586 | 0.03 | 0.03 | −0.29 | 0.40 | 0.54 | 898 |
| NM_003102.1 | 0.01 | −0.39 | −0.71 | 0.49 | 0.43 | 899 |
| AI264774 | 0.00 | −0.11 | −0.43 | 0.20 | 0.44 | 900 |
| N90536 | 0.01 | −0.45 | −0.77 | 0.30 | 0.45 | 901 |
| AA404342 | 0.00 | −0.29 | −0.61 | 0.36 | 0.36 | 902 |
| AI373525 | 0.00 | −0.16 | −0.48 | 0.30 | 0.25 | 903 |
| AI579907 | 0.00 | 0.07 | −0.25 | 0.38 | 0.25 | 904 |
| AA279410 | 0.00 | 0.11 | −0.21 | 0.33 | 0.26 | 905 |
| XM_038308 | 0.04 | 0.35 | 0.03 | 0.51 | 0.54 | 906 |
| NM_000879 | 0.02 | −0.01 | −0.33 | 0.37 | 0.52 | 907 |
| NM_001078) | 0.00 | 0.38 | 0.07 | 0.38 | 0.32 | 908 |
| AA781411 | 0.00 | −0.24 | −0.55 | 0.23 | 0.37 | 909 |
| R07171 | 0.00 | −0.16 | −0.48 | 0.34 | 0.37 | 910 |
| AA136273 | 0.00 | −0.10 | −0.41 | 0.26 | 0.32 | 911 |
| AI565469 | 0.01 | −0.06 | −0.37 | 0.32 | 0.41 | 912 |
| AI799767 | 0.00 | −0.12 | −0.44 | 0.35 | 0.36 | 913 |
| AI889554 | 0.00 | −0.08 | −0.39 | 0.34 | 0.36 | 914 |
| AA410301 | 0.01 | 0.77 | 0.46 | 0.35 | 0.42 | 915 |
| AA995114 | 0.04 | 1.09 | 0.79 | 0.67 | 0.40 | 916 |
| AI694444 | 0.00 | −0.40 | −0.71 | 0.26 | 0.35 | 917 |
| T98940 | 0.00 | 0.05 | −0.26 | 0.45 | 0.27 | 918 |
| R16722 | 0.00 | 0.07 | −0.23 | 0.42 | 0.23 | 919 |
| H05436 | 0.00 | 0.40 | 0.10 | 0.34 | 0.33 | 920 |
| R42778 | 0.01 | 0.39 | 0.09 | 0.45 | 0.33 | 921 |
| AI378275 | 0.00 | −0.02 | −0.33 | 0.29 | 0.40 | 922 |
| XM_083833 | 0.03 | 0.50 | 0.20 | 0.57 | 0.39 | 923 |
| R94894 | 0.03 | 1.00 | 0.70 | 0.35 | 0.55 | 924 |
| H15677 | 0.01 | −0.24 | −0.54 | 0.34 | 0.45 | 925 |
| AI625523 | 0.04 | 0.75 | 0.45 | 0.47 | 0.51 | 926 |
| AI627286 | 0.00 | 0.03 | −0.27 | 0.35 | 0.26 | 927 |
| NM_003807 | 0.01 | 0.08 | −0.22 | 0.35 | 0.42 | 928 |
| NM_002757 | 0.02 | 0.00 | −0.30 | 0.50 | 0.41 | 929 |
| XM_008411 | 0.02 | −0.47 | −0.77 | 0.31 | 0.51 | 930 |
| AI379294 | 0.01 | −0.06 | −0.35 | 0.45 | 0.32 | 931 |
| AI824470 | 0.00 | −0.20 | −0.49 | 0.19 | 0.42 | 932 |
| N94525 | 0.00 | 0.15 | −0.14 | 0.26 | 0.28 | 933 |
| R38432 | 0.01 | −0.03 | −0.32 | 0.27 | 0.41 | 934 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| | | Group of patients with non-infectious MOF | Group of patients with infectious MOF | Group of patients with non-infectious MOF | Group of patients with infectious MOF | |
|---|---|---|---|---|---|---|
| NM_017436.2 | 0.02 | −0.44 | −0.74 | 0.42 | 0.44 | 935 |
| AA398968 | 0.00 | −0.03 | −0.33 | 0.37 | 0.35 | 936 |
| U15085 | 0.03 | −0.89 | −1.18 | 0.47 | 0.47 | 937 |
| AI734941 | 0.01 | −0.14 | −0.43 | 0.31 | 0.41 | 938 |
| AI819159 | 0.00 | 0.44 | 0.15 | 0.39 | 0.28 | 939 |
| AA426024 | 0.02 | −0.11 | −0.40 | 0.46 | 0.42 | 940 |
| AA435854 | 0.00 | −0.33 | −0.62 | 0.21 | 0.28 | 941 |
| NM_003264 | 0.00 | 0.28 | −0.01 | 0.30 | 0.38 | 942 |
| NM_001622.1 | 0.04 | 0.01 | −0.28 | 0.41 | 0.53 | 943 |
| AI828714 | 0.04 | −0.25 | −0.55 | 0.33 | 0.54 | 944 |
| NM_006610 | 0.00 | −0.04 | −0.33 | 0.23 | 0.30 | 945 |
| AI143013 | 0.00 | −0.04 | −0.33 | 0.38 | 0.31 | 946 |
| AA428992 | 0.01 | 0.50 | 0.21 | 0.48 | 0.24 | 947 |
| R40560 | 0.02 | 0.17 | −0.12 | 0.33 | 0.44 | 948 |
| AI203091 | 0.02 | −0.44 | −0.73 | 0.28 | 0.50 | 949 |
| T92041 | 0.00 | 0.07 | −0.22 | 0.28 | 0.22 | 950 |
| AA453794 | 0.00 | 0.20 | −0.09 | 0.22 | 0.29 | 951 |
| R05804 | 0.00 | 0.18 | −0.11 | 0.22 | 0.34 | 952 |
| AA453489 | 0.01 | −0.56 | −0.85 | 0.33 | 0.37 | 953 |
| NM_006664 | 0.00 | 0.67 | 0.39 | 0.30 | 0.35 | 954 |
| AA281330 | 0.03 | 0.76 | 0.48 | 0.57 | 0.38 | 955 |
| AA452139 | 0.00 | 0.08 | −0.20 | 0.31 | 0.24 | 956 |
| R43204 | 0.00 | 0.19 | −0.09 | 0.38 | 0.21 | 957 |
| NM_012340 | 0.01 | 0.05 | −0.24 | 0.36 | 0.40 | 958 |
| NM_004778 | 0.02 | 0.00 | −0.28 | 0.43 | 0.40 | 959 |
| AA490815 | 0.01 | 0.04 | −0.24 | 0.26 | 0.44 | 960 |
| NM_022740 | 0.00 | 0.47 | 0.19 | 0.30 | 0.31 | 961 |
| AI167874 | 0.01 | 0.33 | 0.05 | 0.41 | 0.33 | 962 |
| AA149968 | 0.00 | −0.09 | −0.37 | 0.28 | 0.27 | 963 |
| XM_058179 | 0.03 | −0.04 | −0.32 | 0.58 | 0.35 | 964 |
| R07502 | 0.00 | −0.42 | −0.70 | 0.33 | 0.31 | 965 |
| NM_000752 | 0.01 | −0.27 | −0.56 | 0.48 | 0.29 | 966 |
| XM_003529 | 0.01 | 0.22 | −0.06 | 0.42 | 0.38 | 967 |
| N64541 | 0.01 | 0.13 | −0.15 | 0.44 | 0.37 | 968 |
| NM_001054 | 0.01 | 0.18 | −0.10 | 0.32 | 0.40 | 969 |
| AI499407 | 0.00 | 0.00 | −0.28 | 0.30 | 0.27 | 970 |
| NM_020056 | 0.00 | −0.05 | −0.33 | 0.32 | 0.28 | 971 |
| AA004952 | 0.01 | −0.20 | −0.48 | 0.41 | 0.31 | 972 |
| AI624610 | 0.01 | 0.09 | −0.19 | 0.34 | 0.38 | 973 |
| AA421924 | 0.04 | 0.92 | 0.64 | 0.49 | 0.44 | 974 |
| AI732550 | 0.04 | 0.03 | −0.25 | 0.51 | 0.43 | 975 |
| AI374599 | 0.02 | −0.15 | −0.43 | 0.24 | 0.47 | 976 |
| AI582909 | 0.00 | 0.34 | 0.06 | 0.21 | 0.21 | 977 |
| AI554111 | 0.00 | 0.21 | −0.07 | 0.39 | 0.21 | 978 |
| NM_001734 | 0.00 | −0.21 | −0.49 | 0.21 | 0.37 | 979 |
| AA810014 | 0.03 | 0.23 | −0.05 | 0.56 | 0.33 | 980 |
| AI373295 | 0.00 | 0.32 | 0.05 | 0.31 | 0.23 | 981 |
| XM_048555 | 0.01 | −0.20 | −0.48 | 0.38 | 0.34 | 982 |
| AA435627 | 0.00 | 0.15 | −0.13 | 0.31 | 0.26 | 983 |
| T95815 | 0.00 | 0.55 | 0.27 | 0.33 | 0.32 | 984 |
| AA426030 | 0.03 | −0.14 | −0.42 | 0.40 | 0.42 | 985 |
| AI720051 | 0.01 | −0.29 | −0.56 | 0.30 | 0.43 | 986 |
| AI278521 | 0.01 | −0.50 | −0.77 | 0.39 | 0.34 | 987 |
| N93236 | 0.01 | 0.38 | 0.10 | 0.38 | 0.34 | 988 |
| NM_015645 | 0.03 | −0.28 | −0.55 | 0.44 | 0.43 | 989 |
| AI671360 | 0.00 | 0.22 | −0.05 | 0.28 | 0.28 | 990 |
| T83666 | 0.00 | 0.13 | −0.14 | 0.36 | 0.21 | 991 |
| W02063 | 0.00 | −0.02 | −0.30 | 0.31 | 0.31 | 992 |
| AI659563 | 0.00 | 0.01 | −0.26 | 0.27 | 0.21 | 993 |
| NM_139046 | 0.02 | −0.47 | −0.74 | 0.35 | 0.45 | 994 |
| AA155745 | 0.00 | 0.00 | −0.27 | 0.31 | 0.26 | 995 |
| H40035 | 0.01 | −0.32 | −0.59 | 0.28 | 0.38 | 996 |
| AA101379 | 0.00 | 0.26 | −0.02 | 0.35 | 0.31 | 997 |
| H16790 | 0.00 | 0.22 | −0.05 | 0.37 | 0.28 | 998 |
| AA011511 | 0.02 | −0.29 | −0.55 | 0.32 | 0.41 | 999 |
| AA746495 | 0.05 | 0.17 | −0.10 | 0.56 | 0.39 | 1000 |
| AA845015 | 0.00 | −0.04 | −0.30 | 0.34 | 0.26 | 1001 |
| NM_138636 | 0.05 | 0.51 | 0.24 | 0.39 | 0.52 | 1002 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| NM_033358 | 0.01 | 0.50 | 0.24 | 0.37 | 0.37 | 1003 |
| AI650349 | 0.02 | −0.13 | −0.39 | 0.40 | 0.41 | 1004 |
| NM_001764 | 0.01 | 0.33 | 0.06 | 0.46 | 0.20 | 1005 |
| XM_006447 | 0.03 | −0.53 | −0.80 | 0.49 | 0.39 | 1006 |
| R07185 | 0.00 | 0.12 | −0.14 | 0.34 | 0.22 | 1007 |
| AA187437 | 0.00 | −0.01 | −0.27 | 0.21 | 0.26 | 1008 |
| AI621365 | 0.00 | 0.25 | −0.02 | 0.34 | 0.28 | 1009 |
| NM_020205 | 0.03 | 0.16 | −0.10 | 0.29 | 0.48 | 1010 |
| AI888390 | 0.01 | −0.89 | −1.15 | 0.31 | 0.40 | 1011 |
| AI674699 | 0.01 | −0.09 | −0.35 | 0.34 | 0.37 | 1012 |
| AI620249 | 0.02 | 0.02 | −0.24 | 0.49 | 0.27 | 1013 |
| NM_033295 | 0.02 | −0.32 | −0.58 | 0.41 | 0.39 | 1014 |
| NM_015718.1 | 0.00 | −0.08 | −0.34 | 0.23 | 0.34 | 1015 |
| N73572 | 0.05 | 0.05 | −0.21 | 0.45 | 0.42 | 1016 |
| AI420037 | 0.02 | 0.04 | −0.22 | 0.46 | 0.31 | 1017 |
| AI684431 | 0.00 | 0.28 | 0.03 | 0.32 | 0.27 | 1018 |
| AA017263 | 0.00 | 0.11 | −0.14 | 0.38 | 0.25 | 1019 |
| R45118 | 0.01 | 0.16 | −0.10 | 0.32 | 0.33 | 1020 |
| AI267659 | 0.04 | 0.01 | −0.25 | 0.21 | 0.53 | 1021 |
| AA406083 | 0.03 | 0.00 | −0.26 | 0.38 | 0.41 | 1022 |
| W48664 | 0.00 | 0.21 | −0.05 | 0.31 | 0.22 | 1023 |
| AA514450 | 0.00 | −0.38 | −0.63 | 0.26 | 0.33 | 1024 |
| AI150305 | 0.00 | 0.30 | 0.04 | 0.23 | 0.32 | 1025 |
| AA481504 | 0.03 | −0.74 | −0.99 | 0.37 | 0.42 | 1026 |
| R44840 | 0.02 | 0.22 | −0.04 | 0.45 | 0.32 | 1027 |
| AI160757 | 0.00 | 0.21 | −0.05 | 0.29 | 0.29 | 1028 |
| AA040870 | 0.00 | 0.24 | −0.02 | 0.30 | 0.30 | 1029 |
| AI342905 | 0.02 | 0.49 | 0.24 | 0.43 | 0.35 | 1030 |
| N68463 | 0.05 | 0.09 | −0.16 | 0.46 | 0.43 | 1031 |
| AA398760 | 0.00 | 0.05 | −0.20 | 0.24 | 0.23 | 1032 |
| AI798514 | 0.00 | 0.26 | 0.00 | 0.30 | 0.25 | 1033 |
| AI081725 | 0.00 | 0.18 | −0.07 | 0.31 | 0.28 | 1034 |
| AI799385 | 0.03 | 0.44 | 0.19 | 0.45 | 0.37 | 1035 |
| AA897543 | 0.04 | −0.24 | −0.49 | 0.28 | 0.49 | 1036 |
| N79807 | 0.01 | 0.18 | −0.07 | 0.33 | 0.33 | 1037 |
| AI676097 | 0.05 | 0.21 | −0.04 | 0.57 | 0.32 | 1038 |
| R46372 | 0.01 | 0.02 | −0.23 | 0.28 | 0.37 | 1039 |
| AA448817 | 0.00 | 0.26 | 0.01 | 0.28 | 0.27 | 1040 |
| AI810161 | 0.01 | 0.09 | −0.16 | 0.31 | 0.38 | 1041 |
| H80437 | 0.00 | 0.18 | −0.07 | 0.23 | 0.29 | 1042 |
| AA443664 | 0.00 | −0.02 | −0.27 | 0.29 | 0.27 | 1043 |
| NM_002957.3 | 0.01 | −0.12 | −0.37 | 0.24 | 0.37 | 1044 |
| N69363 | 0.03 | −0.35 | −0.59 | 0.37 | 0.40 | 1045 |
| NM_000552.2 | 0.01 | −0.11 | −0.36 | 0.25 | 0.34 | 1046 |
| AA455080 | 0.01 | 0.08 | −0.16 | 0.34 | 0.28 | 1047 |
| W32272 | 0.00 | −0.25 | −0.50 | 0.26 | 0.30 | 1048 |
| H38087 | 0.04 | 0.76 | 0.51 | 0.34 | 0.47 | 1049 |
| AA504336 | 0.01 | 0.26 | 0.02 | 0.32 | 0.33 | 1050 |
| H04977 | 0.00 | 0.45 | 0.21 | 0.28 | 0.28 | 1051 |
| NM_002670 | 0.05 | 0.19 | −0.06 | 0.32 | 0.50 | 1052 |
| R09417 | 0.02 | −0.07 | −0.32 | 0.31 | 0.41 | 1053 |
| AA040057 | 0.02 | −0.05 | −0.29 | 0.35 | 0.37 | 1054 |
| AI263210 | 0.01 | −0.10 | −0.34 | 0.27 | 0.33 | 1055 |
| AI264626 | 0.01 | −0.12 | −0.37 | 0.33 | 0.29 | 1056 |
| AI478847 | 0.02 | 0.11 | −0.13 | 0.34 | 0.40 | 1057 |
| AI744042 | 0.03 | −0.37 | −0.61 | 0.51 | 0.27 | 1058 |
| AA682790 | 0.02 | 0.01 | −0.23 | 0.32 | 0.40 | 1059 |
| AA629051 | 0.01 | 0.28 | 0.04 | 0.32 | 0.29 | 1060 |
| AI560242 | 0.02 | −0.23 | −0.47 | 0.36 | 0.34 | 1061 |
| AA035428 | 0.01 | −0.14 | −0.38 | 0.26 | 0.32 | 1062 |
| NM_014326 | 0.02 | 0.11 | −0.13 | 0.52 | 0.15 | 1063 |
| AI632740 | 0.01 | −0.16 | −0.40 | 0.31 | 0.30 | 1064 |
| AI130878 | 0.01 | 0.27 | 0.03 | 0.32 | 0.31 | 1065 |
| AI933013 | 0.01 | 0.31 | 0.07 | 0.35 | 0.26 | 1066 |
| AI086719 | 0.01 | 0.00 | −0.24 | 0.37 | 0.24 | 1067 |
| R16568 | 0.03 | 0.10 | −0.14 | 0.24 | 0.46 | 1068 |
| AA009562 | 0.01 | −0.20 | −0.44 | 0.28 | 0.33 | 1069 |
| AI015069 | 0.01 | 0.04 | −0.20 | 0.32 | 0.34 | 1070 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| AA291486 | 0.02 | −0.26 | −0.49 | 0.31 | 0.36 | 1071 |
| H65288 | 0.03 | −0.13 | −0.37 | 0.26 | 0.46 | 1072 |
| W86767 | 0.02 | 0.07 | −0.17 | 0.20 | 0.42 | 1073 |
| H65331 | 0.01 | 0.55 | 0.31 | 0.33 | 0.33 | 1074 |
| AA478985 | 0.04 | −0.12 | −0.36 | 0.20 | 0.51 | 1075 |
| H11274 | 0.02 | −0.02 | −0.26 | 0.28 | 0.40 | 1076 |
| AA044225 | 0.00 | −0.09 | −0.33 | 0.31 | 0.22 | 1077 |
| AI801415 | 0.00 | −0.08 | −0.32 | 0.32 | 0.23 | 1078 |
| AA846527 | 0.00 | −0.14 | −0.37 | 0.24 | 0.25 | 1079 |
| R56890 | 0.01 | −0.04 | −0.28 | 0.25 | 0.34 | 1080 |
| AI921525 | 0.03 | −0.06 | −0.29 | 0.36 | 0.40 | 1081 |
| AA405485 | 0.02 | 0.11 | −0.13 | 0.40 | 0.33 | 1082 |
| AA845635 | 0.00 | −0.03 | −0.26 | 0.31 | 0.26 | 1083 |
| AI150418 | 0.01 | 0.07 | −0.17 | 0.23 | 0.33 | 1084 |
| XM_049849 | 0.02 | 0.55 | 0.32 | 0.32 | 0.37 | 1085 |
| AA406573 | 0.00 | 0.20 | −0.03 | 0.33 | 0.23 | 1086 |
| AA043930 | 0.01 | −0.26 | −0.49 | 0.27 | 0.35 | 1087 |
| AI125496 | 0.01 | −0.30 | −0.53 | 0.29 | 0.33 | 1088 |
| AI654739 | 0.02 | −0.06 | −0.29 | 0.31 | 0.35 | 1089 |
| AA398320 | 0.01 | −0.32 | −0.56 | 0.37 | 0.30 | 1090 |
| NM_002155 | 0.04 | 0.48 | 0.25 | 0.36 | 0.43 | 1091 |
| AA505872 | 0.01 | 0.71 | 0.48 | 0.31 | 0.34 | 1092 |
| NM_016610 | 0.02 | 0.24 | 0.00 | 0.20 | 0.43 | 1093 |
| AA703200 | 0.00 | −0.13 | −0.36 | 0.26 | 0.29 | 1094 |
| R44493 | 0.00 | 0.04 | −0.19 | 0.24 | 0.23 | 1095 |
| XM_046575 | 0.04 | −0.14 | −0.38 | 0.40 | 0.40 | 1096 |
| AI275613 | 0.03 | 0.24 | 0.00 | 0.44 | 0.30 | 1097 |
| AI308602 | 0.04 | 0.19 | −0.05 | 0.38 | 0.40 | 1098 |
| R44328 | 0.01 | 0.24 | 0.01 | 0.30 | 0.30 | 1099 |
| R00206 | 0.00 | 0.07 | −0.16 | 0.23 | 0.31 | 1100 |
| NM_002456 | 0.01 | 0.02 | −0.21 | 0.37 | 0.25 | 1101 |
| AI699371 | 0.03 | −0.18 | −0.41 | 0.46 | 0.28 | 1102 |
| AA935135 | 0.03 | 0.21 | −0.02 | 0.41 | 0.33 | 1103 |
| AA702529 | 0.02 | 0.06 | −0.17 | 0.40 | 0.27 | 1104 |
| AI568023 | 0.02 | −0.19 | −0.42 | 0.36 | 0.30 | 1105 |
| NM_002768 | 0.01 | −0.65 | −0.88 | 0.27 | 0.31 | 1106 |
| AA687208 | 0.02 | −0.32 | −0.55 | 0.24 | 0.39 | 1107 |
| AI221524 | 0.04 | 0.47 | 0.25 | 0.49 | 0.31 | 1108 |
| AA813007 | 0.01 | 0.09 | −0.13 | 0.24 | 0.33 | 1109 |
| AA421326 | 0.02 | −0.33 | −0.55 | 0.28 | 0.38 | 1110 |
| AA922397 | 0.01 | 0.06 | −0.17 | 0.19 | 0.33 | 1111 |
| R51857 | 0.03 | 0.90 | 0.67 | 0.40 | 0.30 | 1112 |
| NM_006564 | 0.00 | −0.22 | −0.44 | 0.33 | 0.21 | 1113 |
| AA807376 | 0.01 | 0.39 | 0.17 | 0.31 | 0.25 | 1114 |
| AA812763 | 0.04 | −0.45 | −0.68 | 0.36 | 0.37 | 1115 |
| AA528169 | 0.02 | 0.34 | 0.12 | 0.37 | 0.32 | 1116 |
| AI804325 | 0.01 | −0.14 | −0.36 | 0.32 | 0.24 | 1117 |
| T70330 | 0.04 | −0.10 | −0.33 | 0.30 | 0.41 | 1118 |
| NM_001766 | 0.03 | 0.30 | 0.08 | 0.39 | 0.35 | 1119 |
| AI696956 | 0.01 | −0.12 | −0.34 | 0.40 | 0.23 | 1120 |
| AI459174 | 0.01 | −0.05 | −0.27 | 0.30 | 0.25 | 1121 |
| R35639 | 0.01 | −0.03 | −0.25 | 0.17 | 0.37 | 1122 |
| W69774 | 0.01 | −0.02 | −0.24 | 0.21 | 0.30 | 1123 |
| AA054265 | 0.05 | 0.37 | 0.15 | 0.40 | 0.38 | 1124 |
| AI382995 | 0.01 | 0.19 | −0.03 | 0.29 | 0.25 | 1125 |
| AI218303 | 0.01 | 0.00 | −0.22 | 0.31 | 0.26 | 1126 |
| AI624954 | 0.01 | −0.18 | −0.40 | 0.28 | 0.31 | 1127 |
| AA759254 | 0.05 | −0.08 | −0.30 | 0.49 | 0.29 | 1128 |
| AI682979 | 0.02 | 0.03 | −0.19 | 0.22 | 0.37 | 1129 |
| XM_001754 | 0.01 | 0.18 | −0.03 | 0.31 | 0.28 | 1130 |
| AI187401 | 0.00 | −0.01 | −0.23 | 0.21 | 0.22 | 1131 |
| AA452113 | 0.01 | 0.24 | 0.02 | 0.25 | 0.30 | 1132 |
| AI656210 | 0.04 | −0.48 | −0.70 | 0.30 | 0.40 | 1133 |
| N29999 | 0.01 | 0.21 | 0.00 | 0.22 | 0.34 | 1134 |
| N68557 | 0.01 | 0.00 | −0.21 | 0.19 | 0.32 | 1135 |
| AI689672 | 0.02 | −0.08 | −0.29 | 0.42 | 0.19 | 1136 |
| AA730310 | 0.00 | −0.07 | −0.28 | 0.25 | 0.22 | 1137 |
| AI431324 | 0.01 | −0.20 | −0.42 | 0.39 | 0.22 | 1138 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| NM_000066 | 0.04 | −0.11 | −0.32 | 0.31 | 0.40 | 1139 |
| XM_034219 | 0.01 | 0.01 | −0.21 | 0.30 | 0.29 | 1140 |
| R43258 | 0.04 | 0.27 | 0.05 | 0.49 | 0.23 | 1141 |
| AI431293 | 0.00 | 0.07 | −0.15 | 0.25 | 0.22 | 1142 |
| R80259 | 0.04 | −0.49 | −0.70 | 0.22 | 0.38 | 1143 |
| AI126520 | 0.00 | 0.13 | −0.08 | 0.22 | 0.21 | 1144 |
| AA937226 | 0.00 | 0.02 | −0.19 | 0.25 | 0.26 | 1145 |
| AI191762 | 0.03 | −0.22 | −0.43 | 0.30 | 0.36 | 1146 |
| AA400470 | 0.00 | −0.10 | −0.31 | 0.34 | 0.17 | 1147 |
| NM_000063 | 0.01 | −0.17 | −0.38 | 0.29 | 0.23 | 1148 |
| H73962 | 0.01 | −0.11 | −0.32 | 0.22 | 0.30 | 1149 |
| AA626313 | 0.01 | −0.06 | −0.27 | 0.23 | 0.30 | 1150 |
| AI553630 | 0.03 | 0.13 | −0.08 | 0.36 | 0.31 | 1151 |
| NM_000257.1 | 0.01 | 0.37 | 0.16 | 0.29 | 0.25 | 1152 |
| N68456 | 0.03 | 0.33 | 0.12 | 0.27 | 0.36 | 1153 |
| XM_054837 | 0.01 | 0.24 | 0.04 | 0.24 | 0.27 | 1154 |
| AI696558 | 0.04 | −0.49 | −0.70 | 0.38 | 0.33 | 1155 |
| AI299876 | 0.05 | 0.03 | −0.18 | 0.36 | 0.37 | 1156 |
| NM_006378 | 0.03 | 0.65 | 0.44 | 0.28 | 0.36 | 1157 |
| AI376955 | 0.02 | −0.56 | −0.76 | 0.31 | 0.33 | 1158 |
| AA025573 | 0.01 | −0.24 | −0.45 | 0.33 | 0.25 | 1159 |
| T99196 | 0.02 | 0.14 | −0.07 | 0.34 | 0.29 | 1160 |
| XM_005637 | 0.05 | 0.25 | 0.05 | 0.19 | 0.45 | 1161 |
| AI597729 | 0.04 | −0.01 | −0.21 | 0.24 | 0.41 | 1162 |
| H78135 | 0.02 | 0.04 | −0.17 | 0.29 | 0.33 | 1163 |
| AI695029 | 0.01 | 0.04 | −0.16 | 0.27 | 0.25 | 1164 |
| AA004279 | 0.02 | −0.18 | −0.39 | 0.21 | 0.34 | 1165 |
| AA844020 | 0.03 | 0.33 | 0.12 | 0.30 | 0.33 | 1166 |
| AI332536 | 0.00 | −0.12 | −0.33 | 0.20 | 0.18 | 1167 |
| AI383368 | 0.03 | −0.40 | −0.61 | 0.21 | 0.38 | 1168 |
| AA423883 | 0.00 | −0.06 | −0.26 | 0.17 | 0.28 | 1169 |
| R36006 | 0.02 | −0.06 | −0.26 | 0.30 | 0.29 | 1170 |
| AI911837 | 0.02 | −0.05 | −0.26 | 0.30 | 0.31 | 1171 |
| AI696820 | 0.03 | −0.37 | −0.57 | 0.32 | 0.34 | 1172 |
| H30516 | 0.02 | −0.17 | −0.37 | 0.22 | 0.34 | 1173 |
| AI926561 | 0.01 | 0.02 | −0.18 | 0.37 | 0.20 | 1174 |
| H61449 | 0.02 | −0.25 | −0.45 | 0.24 | 0.32 | 1175 |
| AA410338 | 0.02 | −0.18 | −0.38 | 0.37 | 0.26 | 1176 |
| AA485229 | 0.00 | 0.05 | −0.15 | 0.18 | 0.18 | 1177 |
| AA044828 | 0.01 | −0.01 | −0.21 | 0.22 | 0.31 | 1178 |
| R07278 | 0.03 | 0.00 | −0.20 | 0.15 | 0.39 | 1179 |
| AI687656 | 0.02 | −0.22 | −0.42 | 0.28 | 0.28 | 1180 |
| AI912316 | 0.03 | 0.21 | 0.01 | 0.42 | 0.24 | 1181 |
| AA017301 | 0.00 | −0.07 | −0.27 | 0.18 | 0.26 | 1182 |
| AA059314 | 0.05 | 0.13 | −0.07 | 0.26 | 0.40 | 1183 |
| NM_024302.2 | 0.04 | 0.20 | 0.00 | 0.29 | 0.35 | 1184 |
| AA446463 | 0.02 | −0.15 | −0.34 | 0.29 | 0.29 | 1185 |
| NM_002747 | 0.01 | 0.19 | −0.01 | 0.24 | 0.24 | 1186 |
| AA446316 | 0.02 | 0.03 | −0.17 | 0.30 | 0.29 | 1187 |
| NM_052813) | 0.05 | −0.22 | −0.42 | 0.39 | 0.30 | 1188 |
| AA731532 | 0.00 | −0.24 | −0.43 | 0.18 | 0.24 | 1189 |
| R00307 | 0.04 | 0.16 | −0.03 | 0.45 | 0.20 | 1190 |
| AI924296 | 0.03 | −0.08 | −0.28 | 0.19 | 0.36 | 1191 |
| AI017741 | 0.01 | 0.07 | −0.12 | 0.29 | 0.21 | 1192 |
| AI619681 | 0.01 | −0.18 | −0.37 | 0.17 | 0.29 | 1193 |
| AA400967 | 0.01 | 0.25 | 0.06 | 0.30 | 0.22 | 1194 |
| NM_000680.1 | 0.01 | 0.28 | 0.09 | 0.20 | 0.28 | 1195 |
| AI732878 | 0.00 | −0.09 | −0.28 | 0.16 | 0.16 | 1196 |
| XM_006454 | 0.02 | −0.08 | −0.27 | 0.34 | 0.24 | 1197 |
| AI688916 | 0.03 | 0.02 | −0.17 | 0.32 | 0.29 | 1198 |
| T79834 | 0.01 | 0.09 | −0.10 | 0.25 | 0.27 | 1199 |
| AI015693 | 0.01 | −0.01 | −0.20 | 0.20 | 0.27 | 1200 |
| R50755 | 0.00 | −0.01 | −0.20 | 0.19 | 0.19 | 1201 |
| W44337 | 0.04 | 0.05 | −0.13 | 0.18 | 0.39 | 1202 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| H23267 | 0.03 | −0.37 | −0.55 | 0.26 | 0.31 | 1203 |
| AA101850 | 0.02 | −0.12 | −0.30 | 0.34 | 0.21 | 1204 |
| AI628322 | 0.05 | −0.03 | −0.22 | 0.37 | 0.28 | 1205 |
| R94207 | 0.02 | 0.13 | −0.06 | 0.26 | 0.28 | 1206 |
| NM_004347 | 0.03 | 0.32 | 0.14 | 0.35 | 0.27 | 1207 |
| AA960802 | 0.05 | 0.14 | −0.04 | 0.37 | 0.29 | 1208 |
| NM_052962 | 0.02 | −0.42 | −0.60 | 0.26 | 0.25 | 1209 |
| T91946 | 0.04 | 0.14 | −0.05 | 0.29 | 0.33 | 1210 |
| AA531564 | 0.04 | −0.14 | −0.32 | 0.37 | 0.26 | 1211 |
| R96155 | 0.01 | 0.00 | −0.18 | 0.28 | 0.21 | 1212 |
| AI825491 | 0.02 | −0.07 | −0.25 | 0.19 | 0.29 | 1213 |
| N53973 | 0.02 | 0.01 | −0.17 | 0.22 | 0.31 | 1214 |
| NM_001544 | 0.01 | 0.10 | −0.08 | 0.27 | 0.22 | 1215 |
| AA702731 | 0.00 | −0.16 | −0.34 | 0.19 | 0.23 | 1216 |
| AI554655 | 0.05 | −0.04 | −0.22 | 0.23 | 0.36 | 1217 |
| H17495 | 0.04 | 0.50 | 0.32 | 0.29 | 0.31 | 1218 |
| AI209185 | 0.02 | −0.24 | −0.42 | 0.16 | 0.31 | 1219 |
| AA031813 | 0.03 | −0.15 | −0.33 | 0.29 | 0.27 | 1220 |
| NM_004166 | 0.04 | −0.37 | −0.54 | 0.35 | 0.27 | 1221 |
| AA461044 | 0.02 | 0.06 | −0.11 | 0.21 | 0.31 | 1222 |
| N45328 | 0.05 | −0.12 | −0.29 | 0.32 | 0.30 | 1223 |
| N64446 | 0.03 | −0.24 | −0.42 | 0.24 | 0.32 | 1224 |
| AI633617 | 0.01 | −0.05 | −0.22 | 0.23 | 0.24 | 1225 |
| R45159 | 0.03 | 0.22 | 0.05 | 0.32 | 0.24 | 1226 |
| R60898 | 0.00 | 0.13 | −0.04 | 0.18 | 0.17 | 1227 |
| AI621170 | 0.03 | −0.05 | −0.22 | 0.30 | 0.27 | 1228 |
| N99049 | 0.01 | 0.16 | −0.01 | 0.31 | 0.19 | 1229 |
| H18651 | 0.01 | 0.19 | 0.02 | 0.24 | 0.22 | 1230 |
| AA568582 | 0.04 | 0.02 | −0.15 | 0.30 | 0.28 | 1231 |
| AA026871 | 0.03 | −0.02 | −0.19 | 0.37 | 0.20 | 1232 |
| AI559626 | 0.01 | −0.11 | −0.28 | 0.23 | 0.21 | 1233 |
| AA443545 | 0.03 | 0.46 | 0.29 | 0.27 | 0.28 | 1234 |
| R43339 | 0.04 | 0.22 | 0.06 | 0.36 | 0.23 | 1235 |
| AA007369 | 0.04 | −0.16 | −0.33 | 0.28 | 0.30 | 1236 |
| AA960982 | 0.01 | 0.25 | 0.08 | 0.26 | 0.22 | 1237 |
| AA481399 | 0.01 | 0.01 | −0.16 | 0.30 | 0.18 | 1238 |
| AA280005 | 0.02 | −0.17 | −0.34 | 0.23 | 0.26 | 1239 |
| NM_005666 | 0.01 | 0.36 | 0.19 | 0.26 | 0.20 | 1240 |
| NM_000491 | 0.03 | 0.08 | −0.09 | 0.32 | 0.24 | 1241 |
| AA844053 | 0.03 | −0.12 | −0.28 | 0.22 | 0.26 | 1242 |
| R49384 | 0.01 | −0.05 | −0.22 | 0.24 | 0.21 | 1243 |
| AI698289 | 0.01 | −0.16 | −0.33 | 0.23 | 0.21 | 1244 |
| AI680467 | 0.04 | −0.09 | −0.26 | 0.23 | 0.31 | 1245 |
| M90391 | 0.03 | −0.11 | −0.28 | 0.27 | 0.23 | 1246 |
| AF218727 | 0.05 | 0.18 | 0.02 | 0.25 | 0.31 | 1247 |
| H22946 | 0.04 | −0.44 | −0.60 | 0.27 | 0.29 | 1248 |
| N49285 | 0.03 | −0.51 | −0.67 | 0.23 | 0.28 | 1249 |
| N74903 | 0.01 | 0.17 | 0.01 | 0.21 | 0.22 | 1250 |
| NM_001066.2 | 0.04 | 0.14 | −0.02 | 0.23 | 0.30 | 1251 |
| NM_021805 | 0.02 | 0.05 | −0.11 | 0.29 | 0.21 | 1252 |
| NM_004590 | 0.04 | 0.26 | 0.10 | 0.27 | 0.27 | 1253 |
| AA482392 | 0.01 | −0.19 | −0.35 | 0.25 | 0.20 | 1254 |
| AA131826 | 0.01 | −0.04 | −0.20 | 0.26 | 0.17 | 1255 |
| AA947111 | 0.02 | 0.07 | −0.09 | 0.17 | 0.27 | 1256 |
| AI159796 | 0.04 | −0.13 | −0.28 | 0.20 | 0.28 | 1257 |
| AF086537 | 0.05 | 0.15 | −0.01 | 0.32 | 0.24 | 1258 |
| AI147932 | 0.00 | 0.13 | −0.03 | 0.23 | 0.16 | 1259 |
| AA460956 | 0.04 | 0.11 | −0.04 | 0.30 | 0.24 | 1260 |
| AA398249 | 0.03 | −0.11 | −0.27 | 0.23 | 0.26 | 1261 |

TABLE 4-continued

Significantly reduced gene activities in samples of patients with infectious MOF, if compared with the gene activites of patients with non-infectious MOF.

| GenBank Accession No. | p-value | Mean normalised and transformed expression value | | Standard deviation | | SEQUENCE-ID |
| --- | --- | --- | --- | --- | --- | --- |
| | | Group of patients with non-infectious MOF | Group of patients with infectious MOF | Group of patients with non-infectious MOF | Group of patients with infectious MOF | |
| H08161 | 0.04 | −0.23 | −0.39 | 0.23 | 0.28 | 1262 |
| AA281734 | 0.03 | −0.12 | −0.28 | 0.31 | 0.19 | 1263 |
| AA628488 | 0.04 | −0.18 | −0.33 | 0.20 | 0.30 | 1264 |
| AA430519 | 0.04 | −0.06 | −0.21 | 0.22 | 0.26 | 1265 |
| AA468113 | 0.05 | −0.16 | −0.31 | 0.29 | 0.25 | 1266 |
| AI424466 | 0.04 | 0.06 | −0.10 | 0.26 | 0.24 | 1267 |
| AI190760 | 0.04 | 0.04 | −0.11 | 0.29 | 0.23 | 1268 |
| N89992 | 0.01 | −0.06 | −0.21 | 0.23 | 0.18 | 1269 |
| AA046092 | 0.01 | 0.10 | −0.05 | 0.16 | 0.21 | 1270 |
| W35358 | 0.02 | 0.05 | −0.10 | 0.22 | 0.20 | 1271 |
| AA398341 | 0.04 | −0.19 | −0.33 | 0.27 | 0.23 | 1272 |
| H01969 | 0.05 | −0.09 | −0.24 | 0.32 | 0.20 | 1273 |
| AA970008 | 0.05 | −0.34 | −0.48 | 0.32 | 0.21 | 1274 |
| R89846 | 0.01 | 0.14 | −0.01 | 0.20 | 0.20 | 1275 |
| H18639 | 0.04 | 0.13 | −0.02 | 0.26 | 0.24 | 1276 |
| AI016342 | 0.02 | 0.02 | −0.12 | 0.18 | 0.22 | 1277 |
| NM_002184 | 0.04 | −0.23 | −0.37 | 0.17 | 0.28 | 1278 |
| NM_001643.1 | 0.03 | 0.13 | −0.01 | 0.19 | 0.26 | 1279 |
| AA280029 | 0.04 | −0.14 | −0.28 | 0.28 | 0.22 | 1280 |
| AA927949 | 0.00 | 0.17 | 0.02 | 0.16 | 0.14 | 1281 |
| AA625552 | 0.04 | 0.05 | −0.09 | 0.28 | 0.20 | 1282 |
| AA458912 | 0.03 | −0.23 | −0.37 | 0.24 | 0.23 | 1283 |
| AI188025 | 0.02 | 0.29 | 0.15 | 0.21 | 0.22 | 1284 |
| XM_007417 | 0.02 | 0.00 | −0.14 | 0.21 | 0.19 | 1285 |
| AA019529 | 0.03 | −0.29 | −0.42 | 0.22 | 0.22 | 1286 |
| AA401542 | 0.04 | −0.09 | −0.22 | 0.17 | 0.25 | 1287 |
| AI478746 | 0.04 | 0.00 | −0.13 | 0.23 | 0.22 | 1288 |
| AA291522 | 0.01 | −0.33 | −0.47 | 0.14 | 0.22 | 1289 |
| AI493122 | 0.05 | 0.16 | 0.03 | 0.25 | 0.22 | 1290 |
| AI203665 | 0.02 | 0.11 | −0.02 | 0.22 | 0.18 | 1291 |
| R74060 | 0.05 | −0.15 | −0.28 | 0.20 | 0.24 | 1292 |
| AI185721 | 0.04 | −0.25 | −0.37 | 0.22 | 0.19 | 1293 |
| AA437106 | 0.05 | 0.10 | −0.02 | 0.23 | 0.20 | 1294 |
| NM_139208 | 0.04 | −0.07 | −0.18 | 0.22 | 0.20 | 1295 |
| AI922221 | 0.05 | −0.02 | −0.14 | 0.20 | 0.20 | 1296 |
| AA412418 | 0.05 | −0.26 | −0.37 | 0.19 | 0.18 | 1297 |

The GenBank Accession Numbers indicated in Tables 3 and 4 (Internet-access via http://www.ncbi.nlm.nih.gov/) of the individual sequences are associated with the attached sequence listing, itemized or in detail with respectively one sequence (Sequence ID: 1 up through Sequence ID: 1297).

Furthermore, the sequences are individually disclosed therein.

This sequence listing is part of the description of the present invention.

Additionally, these sequences are disclosed in the German patent application No. 102004049897.0, which is incorporated herein by reference.

Generation of Gene Activity Classificators (Training Set)

Figure 2:
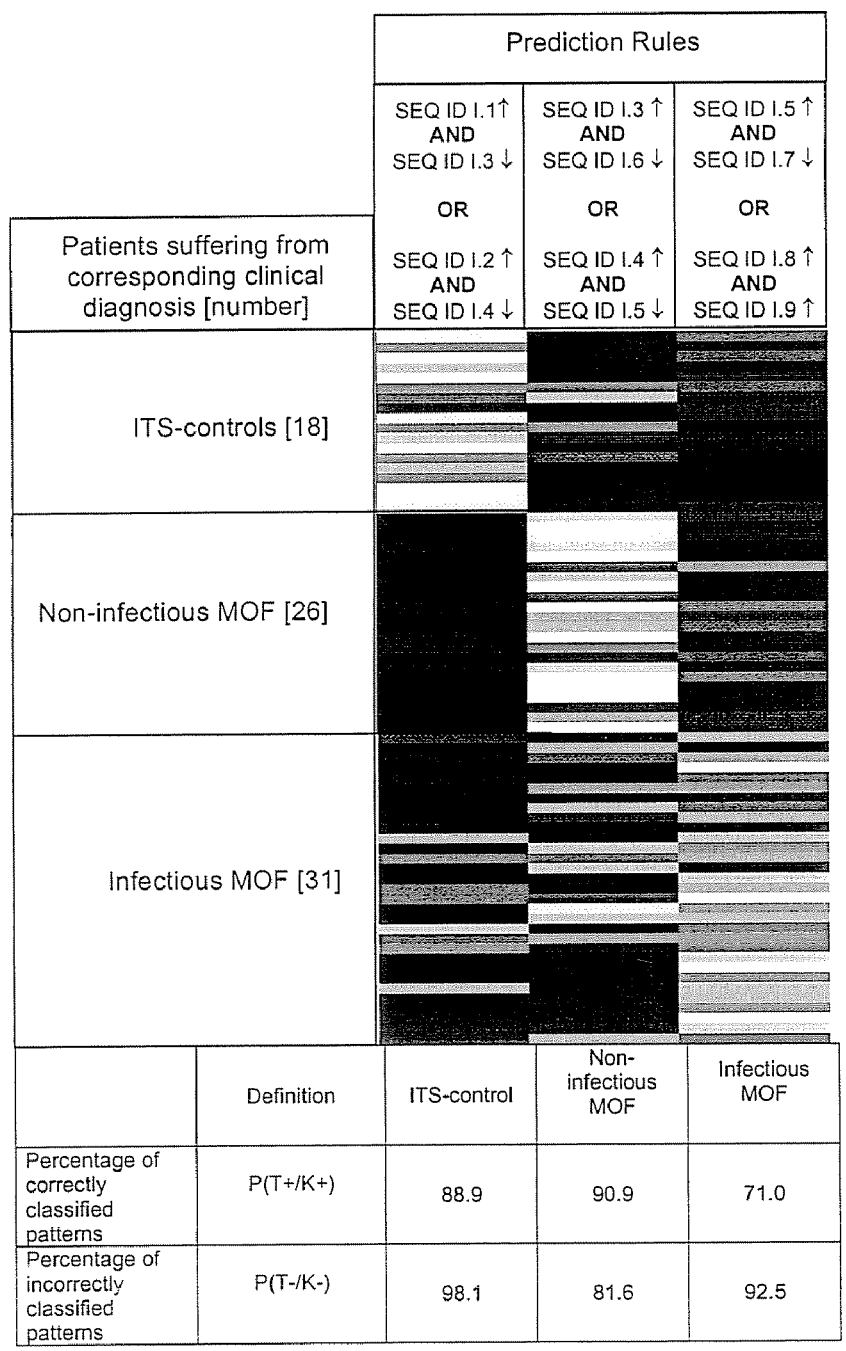
FIG. 2 shows classification of gene expression patterns into the classes infectious MOF and non-infectious MOF by means of the MediPred (Biocontrol Jena GmbH) software.
Figure 3:
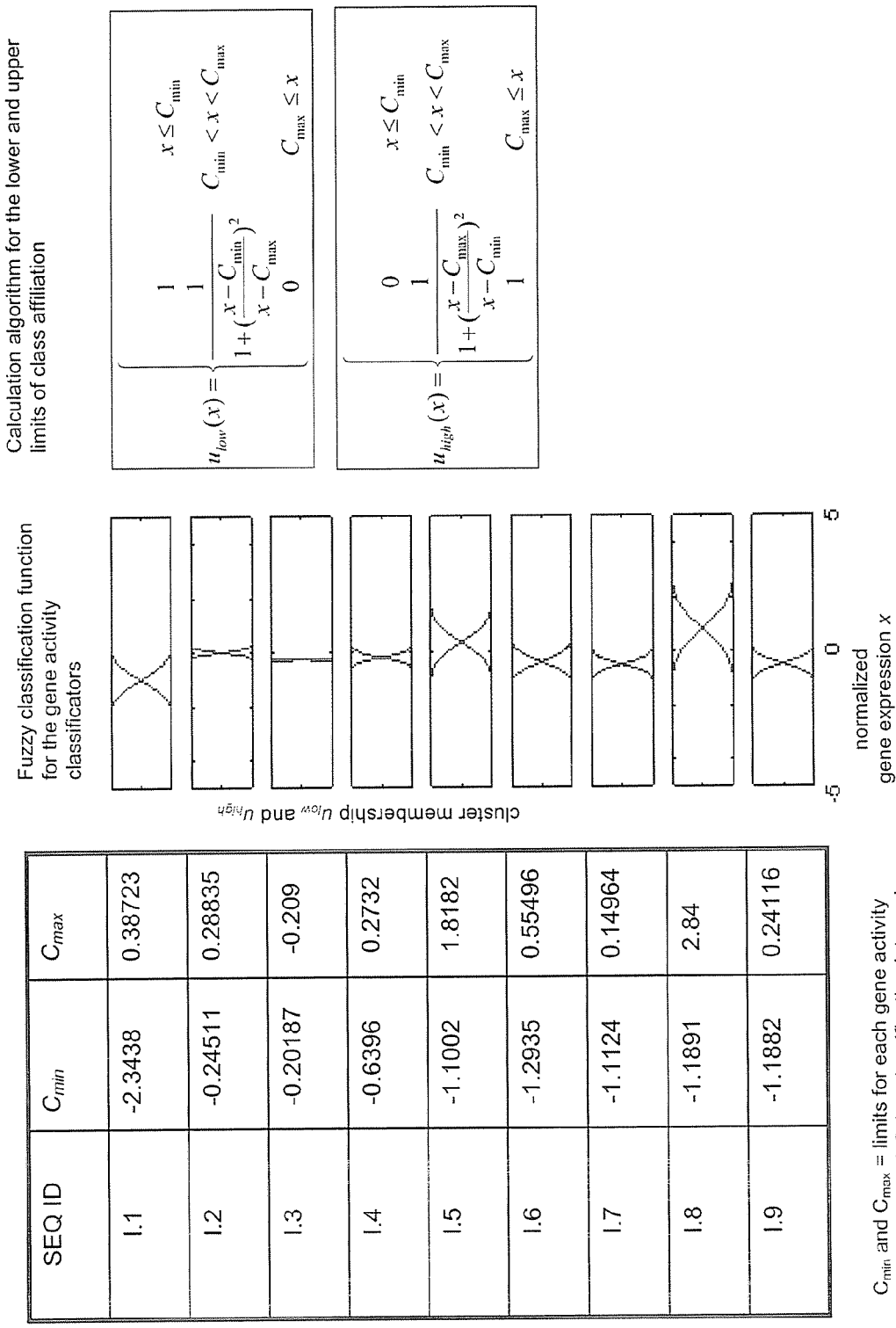
FIG. 3 shows thresholds determined for high and low expression for each gene.

On the basis of all gene activities measured, gene activity classificators and selection rules were established by means of the MediPred (Biocontrol Jena GmbH) software, allowing the classification of gene expression patterns into the classes infectious MOF and non-infectious MOF (FIG. 2). Thresholds were determined for high and low expression for each gene (designated $C_{min}$ and $C_{max}$ in FIG. 3) and genes with typical and robust gene expression behaviors per patient class were extracted.

Testing of Gene Activity Classificators with Gene Expression Profiles not Yet Classified (Test Set)

The determined gene activity classificators were tested using the defined selection rules on a test set of altogether 190 not yet classified gene expression patterns of ITS-controls (56), patients with non-infectious MOF (75) and patients with infectious MOF (59), respectively, and validated by means of clinical data.

For this purpose, gene expression profiles were selected from patients clinically diagnosed as ITS-control or non-infectious MOF or infectious MOF.

If, in the subsequent comparison with the training set, the expression patterns to be classified were found to be the training set and within the expression limits of the corresponding gene activity classificators defined by the selection rules (and the selection criteria simultaneously applied), the expression pattern to be classified was assigned to the corresponding class.

Table 5 shows which test set belongs to which class. As will be seen, 86% of the ITS-controls, 80% of the patients with non-infectious multiple organ failure as well as 63% of the patients with infectious multiple organ failure could be correctly classified into the corresponding class.

TABLE 5

Percentage of 190 gene expression profiles to be classified into the classes ITS-control, non-infectious MOF and infectious MOF.

| Patient groups | | ITS-controls | Non-infectious multiple organ failure | Infectious multiple organ failure |
|---|---|---|---|---|
| Number of gene expression profiles to be classified | | 56 | 75 (several days of 16 patients) | 59 (several days of 35 patients) |
| Corresponding to classes [%] | ITS-controls | 86 | 4 | 14 |
| | Non-infectious multiple organ failure | 13 | 80 | 16 |
| | Infectious multiple organ failure | 2 | 16 | 63 |

This shows that the gene activity classificators in conjunction with the selection criteria are usable for the invention.

REFERENCES

1. Natanson C (1997) Anti-inflammatory therapies to treat sepsis and septic shock: A reassessment. Crit Care Med 25: 1095-1099
2. Geiger K (1995) Fruhparameter für Multiorgandysfunktionssyndrom. in Hartenauer U (ed.) Sepsis in der Frohphase Munchen MMV Medizin Veriag 19-25
3. Knaus W A, Draper E A, Wagner D P, Zimmermann J E (1985) Prognosis in acute organ-system failure. Ann Surg 202: 658-693
4. Goris R I, Bockhorst T P, Nuytinck J K S (1995) Mulitiple organ failure. Arch Surg 120:1109-1115
5. Vincent J L, Moreno R, Takala J, et al. (1996) The SOFA (Sepsis-related Organ Failure Assessment) score to describe organ dysfunction/failure. On behalf of the Working Group on Sepsis-Related Problems of the European Society of Intensive Care Medicine, Intensive Care Med. July 22(7):707-10.
6. Pfeiffer L, Ehrhardt N, Kretschmar R, et al. (1996) Endotoxinamie und Multiorganversagen nach Polytrauma. Anaesthesiol Reanimat 21: 91-96
7. Schlag G, Redl H (1993) Organ in shock, early organ failure, late organ failure, in Schlag G and Redl H (eds.) Pathophysiology of shock, sepsis, and organ failure Berlin Heidelberg Springer-Verlag, 1-4
8. Bone R C, Balk R A, Cerra F B, et al. (1992) The ACCP/SCCM Consensus Conference Committee (1992) Definitions for Sepsis and organ failure and guidelines for the use of innovative therapies in Sepsis. Chest 101:1656-1662; und Crit Care Med 1992; 20: 864-874.
9. Levy M M, Fink M, Marshall J C, et al. (2003) For the International Sepsis Definitions Conference: 2001 SCCM/ESICM/ACCP/ATS/SIS International Sepsis Definitions Conference. Crit Care Med. April; 31(4):1250-6
10. http://chirinn.klinikum.uni-muenchen.de/forschung/for_01_14_04.html, Stand Otober 2004, modifiziert
11. Marik P E. (1993) Gastric intramucosal pH. A better predictor of multiorgan dysfuction syndrom and death than oxygen derived variables in patients with sepsis. CHEST 104: 225-229
12. Bernardin G, Pradier C, Tiger F, et al. (1996) Blood pressure and arterial lactate level are early indicators of short-term survival in human septic shock. Intensiv Care Med 22: 17-25;
13. Marecaux G, Pinsky M R, Dupont E, et al. (1996) Blood lactate levels are better prognostic indicators than TNF and IL-6 levels in patients with septic shock. Intensiv Care Med 22: 404-408
14. Duswald K H, Jochum M, Schramm W, Fritz H (1985) Released granulocytic elastase: an indicator of pathobiochemical alterations in septicemia after abdominal surgery. Surgery 98: 892-899
15. Nuytinck J K S, Goris R I, Redl H, et al. (1986) Posttraumatic complications and inflammatory mediators. Arch Surg 121: 886-890
16. Nast-Kolb D, Jochum M, Waydlas C, et al. (1991) Die Wertigkeit biochemischer Faktoren beim Polytrauma. Hefte Unfallheilkunde 215: 215
17. Hack C E, de Groot E R, Felt-Bersma R J, et al. (1989): Increased plasma levels of interleukin-6 in sepsis" Blood 74: 1704-1710
18. Patel R T, Deen K I, Youngs D, et al. (1994) Interleukin 6 is a prognostic indicator of outcome in severe intra-abdominal sepsis. Br J Surg 81:1306-1308
19. Southern E M (1974) An improved method for transferring nucleotides from electrophoresis strips to thin layers of ion-exchange cellulose. Anal Biochem 62:317-318
20. Gillespie D, Spiegelman S (1965) A quantitative assay for DNA-RNA hybrids with DNA immobilized on a membrane. J Mol Biol 12:829-842
21. Lennon G G, Lehrach H (1991) Hybridization analyses of arrayed cDNA libraries. Trends Genet 7: 314-317
22. Kafatos F C, Jones C W, Efstratiadis A (1979) Determination of nucleic acid sequence homologies and relative concentrations by a dot hybridization procedure. Nucl Acid Res 7:1541-1552
23. Fodor S P, Read J L, Pirrung M C, Stryer L, Lu A T, Solas D (1991) Light-directed, spatially addressable parallel chemical synthesis. Science 251:767-773
24. Pease A C, Solas D, Sullivan E J, Cronin M T, Holmes C P, Fodor S P (1994) Light-generated oligonucleotide arrays for rapid DNA sequence analysis. Proc Natl Acad Sci USA 91:5022-5026
25. Schena M, Shalon D, Davis R W, Brown P O (1995) Quantitative monitoring of gene expression patterns with a complementary DNA microarray. Science 270:467-470
26. Golub T R, Slonim D K, Tamayo P, et al. (1999) Molecular classification of cancer: class discovery and class prediction by gene expression monitoring. Science 286:531-537
27. Alizadeh A A, Eisen M B, Davis R E, et al. (2000) Distinct types of diffuse large B-cell lymphoma identified by gene expression profiling. Nature 403:503-51
28. Feezor R J, Baker H V, Xiao W, et al. (2004) Genomic and Proteomic Determinants of outcome in patients undergoing thoracoabdominal aortic aneurysm repair. Journal of Immunology 172 (11): 7103-7109

29. Rademacher md; mCsHANE lm; Simon R (2002) A paradigm for class prediction using gene expression profiles. J. Comput. Biol. 9:505-511
30. Li L, Darden T A, Weinberg C R, Levine A J et al. (2001) Gene assesment and sample classification for gene expression data using a genetic algorith/k-nearest neighbor method. Comb. Chem. High Throuput Screen. 4:727 7-39
31. Zhang H, Yu C-Y, Singer B et al. (2001) Recursive partitioning for tumor classification with gene expression microarray data. Proc. Nat. Acad. Sci. USA 2001, 98:6730-6735
32. Furey T S, Cristianni N, Duffy N (2000) Support vector machine classification and validation of cancer tissue samples using microarray expression data. Bioinf. 16:906-914
33. Simon R M, Korn E L, McShane L et al. (2004) Design and analysis of DNA microarray investigations. Springer-Verlag, New York, ISBN 0-387-00135-2
34. Huber W, Heydebreck A, Sueltmann H, et al. (2003) Parameter estimation for the calibration and variance stabilization of microarray data. Stat. Appl. in Gen. and Mol. Biol. Vol. 2, Issue 1, Article 3

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08236496B2). An electronic copy of the "Sequence Listing" will also be available from the USPTO upon request and payment of the fee set forth in 37 CFR 1.19(b)(3).

The invention claimed is:

1. A method for classifying patients suffering from infectious and non-infectious multiple organ failure, respectively, comprising the following steps:
   (a) isolation of mRNA from a patient sample;
   (b) labeling the mRNA with a detectable unit;
   (c) contacting the labeled mRNA at least two with gene activity markers, said gene activity markers being polynucleotides selected from the group consisting of SEQ ID NO: 1 to 9, or partial sequences thereof having at least 20 nucleotides in length, immobilized on a microarray, so that the individual gene activity markers are separated from each other even after the contacting step;
   (d) washing of the hybridized gene activity markers to remove excess labeled mRNA;
   (e) stimulating the detectable unit so as to emit a signal;
   (f) reading out the hybridization signals for each of the individual gene activity markers and comparing them with a reference sample of a healthy patient, wherein an overexpression of mRNA corresponding to SEQ ID NO: 1 and an underexpression of mRNA corresponding to SEQ ID NO: 3 or an overexpression of mRNA corresponding to SEQ ID NO: 2 and an underexpression of mRNA corresponding to SEQ ID NO: 4 indicates the classification "no infection and without multiple organ failure";
   an overexpression of mRNA corresponding to SEQ ID NO: 3 and an underexpression of mRNA corresponding to SEQ ID NO: 6 or an overexpression of mRNA corresponding to SEQ ID NO: 4 and an underexpression of mRNA corresponding to SEQ ID NO: 5 indicates the classification "non-infectious organ failure"; and
   an overexpression of mRNA corresponding to SEQ ID NO: 5 and an underexpression of mRNA corresponding to SEQ ID NO: 7 or an overexpression of mRNA corresponding to SEQ ID NO: 8 and an underexpression of mRNA corresponding to SEQ ID NO: 9 indicates the classification "infectious multiple organ failure".

2. The method according to claim 1, wherein the patient sample comprises body fluids.

3. The method according to claim 1, wherein the patient sample comprises body fluids selected from blood, liquor, urine, ascitic fluid, seminal fluid, saliva, puncture fluid, cell content, or a mixture thereof.

* * * * *

UNITED STATES PATENT AND TRADEMARK OFFICE
CERTIFICATE OF CORRECTION

PATENT NO.       : 8,236,496 B2
APPLICATION NO.  : 11/909372
DATED            : August 7, 2012
INVENTOR(S)      : Russwurm et al.

Page 1 of 1

It is certified that error appears in the above-identified patent and that said Letters Patent is hereby corrected as shown below:

In the Specification, Col. 51, line 26-28, 2. Geiger K, should read: --

2. Geiger K (1995) Frühparameter für Multiorgandysfunktionssyndrom. in Hartenauer U (ed.) Sepsis in der Frühphase München MMV Medizin Verlag 19-25

In the Claims, Col. 53, line 32-38, on page 53/54, Claim 1, (c) should read: --

(c) contacting the labeled mRNA with at least two gene activity markers, said gene activity markers being polynucleotides selected from the group consisting of SEQ ID NO: 1 to 9, or partial sequences thereof having at least 20 nucleotides in length, immobilized on a microarray, so that the individual gene activity markers are separated from each other even after the contacting step;

Signed and Sealed this
Twenty-fourth Day of September, 2013

Teresa Stanek Rea
*Deputy Director of the United States Patent and Trademark Office*